United States Patent [19]

Kim et al.

[11] 4,454,291

[45] Jun. 12, 1984

[54] N-(2-SUBSTITUTED-1-OXOALKYL)-2,3-DIHYDRO-1H-INDOLE-2-CARBOXYLIC ACID DERIVATIVES

[75] Inventors: Dong H. Kim, Wayne; Ronald J. McCaully, Malvern, both of Pa.

[73] Assignee: American Home Products Corporation, New York, N.Y.

[21] Appl. No.: 391,080

[22] Filed: Jun. 22, 1982

Related U.S. Application Data

[60] Division of Ser. No. 284,433, Jul. 20, 1981, Pat. No. 4,350,633, which is a continuation-in-part of Ser. No. 164,992, Jul. 1, 1980, Pat. No. 4,303,583, which is a continuation-in-part of Ser. No. 065,817, Aug. 13, 1979.

[51] Int. Cl.³ .................................. C07D 209/42
[52] U.S. Cl. .................................... 548/491
[58] Field of Search ........................ 548/491

[56] References Cited

U.S. PATENT DOCUMENTS

| | | | |
|---|---|---|---|
| 3,780,062 | 12/1975 | Kaiser et al. | |
| 3,796,723 | 3/1974 | Kaiser et al. | |
| 4,046,889 | 9/1977 | Ondetti et al. | 260/239 A |
| 4,105,776 | 8/1978 | Ondetti et al. | 260/239 A |
| 4,251,444 | 2/1981 | Freed et al. | 260/244.4 |
| 4,256,751 | 3/1981 | Hayashi et al. | 424/258 |

FOREIGN PATENT DOCUMENTS

| | | |
|---|---|---|
| 0009183 | 1/1980 | European Pat. Off. |
| 0012401 | 6/1980 | European Pat. Off. |
| 2937779 | 4/1981 | Fed. Rep. of Germany |

OTHER PUBLICATIONS

Hackh's Chemical Dictionary, fourth edition, J. Grant, editor, McGraw-Hill, N.Y. (1969), p. 595.
Ondetti, M. A., "Orally Active Angiotensin-Converting Enzyme Inhibitors", Gordon Research Conference-Medicinal Chemistry, Colby-Sawyer College, New London, New Hampshire (Jul. 31-Aug. 4, 1978): Program handout (4 pages).
Soffer et al., "Physiologic, Biochemical, and Immunologic Aspects of Angiotensin-Converting Enzyme", Prog. in Cardiovasc. Diseases, XXI, 167-175 (Nov./Dec., 1978).
Goodman and Gilman, The Pharmacological Basis of Therapeutics, pp. 228-229, (MacMillan Publishing Co., New York, NY, 1975).
Cushman et al., "Design of Potent Competitive Inhibitors of Angiotensin-Converting Enzyme, Carboxyalkanoyl and Mercaptoalkanoyl Amino Acids", Biochemistry, 16, 5484-5491 (1977).
Gavras et al., "Antihypertensive Effect of the Oral Angiotensin Converting-Enzyme Inhibitor SQ 14225 in Man", N. Engl. J. Med., 298, 991-995 (May, 1978).
Wong et al., "The In Vitro Metabolism of ³⁵S-Captopril (SQ 14, 225), An Antihypertensive Agent", The Pharmacologist, 20, 213, Abstract No. 345 (1978).
Laragh, John H., "The Renin System in High Blood Pressure, from Disbelief to Reality: Converting-Enzyme Blockade for Analysis & Treatment", Prog. in Cardiovasc. Diseases, XXI, No. 3, 159-166, (Nov./Dec., 1978).
Oparil, Suzanne, "Angiotensin I Converting Enzyme Inhibitors", Chapter 6.3 in Hypertension (McGraw-Hill, 1977).
Cushman et al., "Design of New Antihypertensive Drugs: Potent and Specific Inhibitors of Antiogensin-Converting Enzyme", Prog. in Cardiovasc. Diseases, XXI, No. 3, 176-182 (Nov./Dec., 1978).

Primary Examiner—Donald G. Daus
Assistant Examiner—M. C. Eakin
Attorney, Agent, or Firm—Arthur G. Seifert

[57] ABSTRACT

Disclosed herein are 2,3-dihydro-1H-indole-2-carboxylic acids substituted on the nitrogen with 3-mercapto-2-alkyl-1-oxoalkyl, 3-phosphoryl-2-alkyl-1-oxopropyl, or 2-amino-2-alkyl-1-oxoalkyl derivatives which act as inhibitors of angiotensin converting enzyme and as antihypertensive agents. The compounds of the invention (excluding disclosed intermediates) have the general formula:

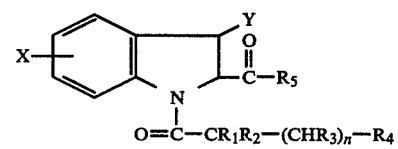

wherein:
n is 1 or 0;
$R_1$ is hydrogen, lower alkyl, aryl or aralkyl;
$R_2$ is hydrogen or lower alkyl;
$R_3$ is hydrogen, lower alkyl or aroyl;
$R_5$ is hydroxy, amino, or lower alkoxy;
X is hydrogen, hydroxy, lower alkyl, lower alkoxy, or halogen;
Y is hydrogen, lower alkyl, or aryl;
Y is hydrogen, lower alkyl, or aryl;
$R_4$ is

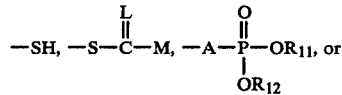

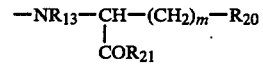

wherein:
L is O, $NR_7$ or S (where $R_7$ is hydrogen or lower alkyl);
M is $R_8$, $OR_8$, $SR_8$, or $NR_9R_{10}$ (where $R_8$ is hydrogen, lower alkyl, aryl, or aralkyl; and $R_9$ and $R_{10}$ are, independently, hydrogen, lower alkyl, or aryl);
A is O, $NR_{13}$ or S;
$R_{11}$ and $R_{12}$ are, independently, hydrogen, alkyl, aralkylor aryl;
$R_{13}$ is hydrogen or lower alkyl;
m is 0, 1, 2, or 3;
$R_{20}$ is hydrogen or aryl; and
$R_{21}$ is hydroxy or lower alkoxy; or pharmaceutically acceptable salts thereof.

11 Claims, No Drawings

N-(2-SUBSTITUTED-1-OXOALKYL)-2,3-DIHYDRO-1H-INDOLE-2-CARBOXYLIC ACID DERIVATIVES

This application is a divisional of Ser. No. 06/284,433, filed July 20, 1981, now U.S. Pat. No. 4,350,633 which is a continuation-in-part of Ser. No. 164,992, filed July 1, 1980, now U.S. Pat. No. 4,303,583 which is a continuation-in-part of Ser. No. 06/065,817, filed Aug. 13, 1979.

This invention concerns 2,3-dihydro-1H-indole-2-carboxylic acids substituted on the nitrogen with 3-mercapto-2-alkyl-1-oxoalkyl, 3-phosphoryl-2-alkyl-1-oxopropyl, or 2-amino-2-alkyl-1-oxoalkyl derivatives, having the formula:

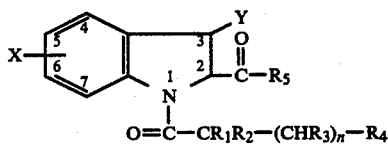

wherein:

n is 1 or 0;

$R_1$ is hydrogen, lower alkyl, aryl, or aralkyl;

$R_2$ is hydrogen or lower alkyl;

$R_3$ is hydrogen, lower alkyl or aroyl;

$R_5$ is hydroxy, amino, or lower alkoxy;

X is hydrogen, hydroxy, lower alkyl, lower alkoxy, or halogen;

Y is hydrogen, lower alkyl, or aryl;

$R_4$ is

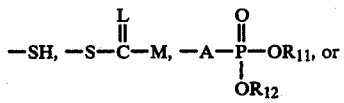

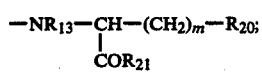

wherein:

L is O, $NR_7$ or S (where $R_7$ is hydrogen or lower alkyl);

M is $R_8$, $OR_8$, $SR_8$, or $NR_9R_{10}$ (where $R_8$ is hydrogen, lower alkyl, aryl, or aralkyl; and $R_9$ and $R_{10}$ are, independently, hydrogen, lower alkyl, or aryl);

$R_{11}$ and $R_{12}$ are, independently, hydrogen, alkyl, aralkyl or aryl;

$R_{13}$ is hydrogen or lower alkyl;

m is 0, 1, 2, or 3;

$R_{20}$ is hydrogen or aryl; and $R_{21}$ is hydroxy or lower alkoxy;

or pharmaceutically acceptable salts thereof.

This invention further concerns 1H, 3H-[1,4]thiazepino[4,3-a]indoles and 1-H-[1,4]thiazino[4,3-a]indoles having the formula:

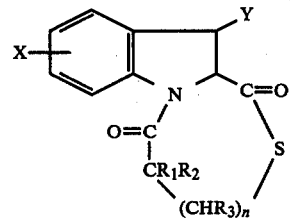

where n, $R_1$, $R_2$, $R_3$, X, and Y are the same as defined for Formula I.

The compounds of Formulas I and II (and disulfides of I) act as inhibitors of angiotensin converting enzyme and are useful as agents for the treatment of hypertension and for the study of the renin-angiotensin-aldosterone system of warm-blooded animals. Also within the scope of the invention are methods of treatment of hypertension utilizing the compounds of the invention, processes for the preparation of the compounds, and intermediate compounds.

As used herein, "lower alkyl" and "lower alkoxy" refer to groups having up to 4 carbon atoms. "Aryl" refers to phenyl or phenyl substituted by a halogen, lower alkyl, or lower alkoxy group. "Aralkyl" refers to benzyl or benzyl substituted as above for phenyl. "Aroyl" refers to benzoyl or benzoyl substituted as above for phenyl. Halogen refers to chlorine, bromine and fluorine.

BACKGROUND OF THE INVENTION

In pharmacological research on hypertension, recent attention has focused on the study of the renin-angiotensin-aldosterone system, and, in particular, on the development of an effective anti-hypertensive agent which would, theoretically, achieve its result by inhibiting the action of angiotensin converting enzyme in converting antiogensin I to angiotensin II. The inhibition of the production of angiotensin II became important because of the discoveries of that angiotensin II is the most potent pressor agent (vasoconstrictor) present in the mammalian body and, in addition, stimulates the adrenal cortex to release aldosterone, thereby causing excessive sodium retention and fluid retention, contributing further to the hypertensive state. Thus, inhibiting the conversion of angiotensin I to angiotensin II is believed to work directly on the primary biochemical mechanisms creating increased blood pressure. For a description of the mechanisms and of the mammalian renal-angiotensin-aldosterone system, see *Hypertension*, Genest et al., ed., Chapters 6.1, 6.2, 7.1, 7.2, and 7.3 (McGraw Hill, 1977) and John H. Laragh, "The Renin System in High Blood Pressure, From Disbelief to Reality: Converting-Enzyme Blockade for Analysis and Treatment", Prog. in Cardio. Vasc. Disease, XXI, No. 3, 159–166 (November, 1978).

An extensive list of angiotensin converting enzyme inhibitors is set forth in Suzanne Oparil's article entitle "Angiotensin I Converting Enzyme and Inhibitors" in Genest et al., supra, Chapter 6.3, at pp. 159–161. These inhibitors are summarized in Table I, p. 161, thereof and include chelating agents, sulfonylating agents, heavy metal ions, sulfhydryl binding reagents, and various peptides. The polypeptides described therein as angiotensin converting enzyme inhibitors include hormones, such as bradykinin; products of substrate digestion such as His-Leu, Phe-Arg, and Arg-Pro-Pro; and various snake venom polypeptide extracts. Two of the most potent and most studied inhibitors are the *Bothrops jararaca* snake venom extract, the pentapeptide (Pyr-Lys-Trp-Ala-Pro), also referred to as BPP$_{5a}$, and the nonapeptide (Pyr-Trp-Pro-Arg-Pro-Gln-Ile-Pro-Pro), also referred to as BPP$_{9a}$. (BPP stands for Bradykinin Potentiating Peptide). BPP$_{9a}$ has been shown to be an effective anti-hypertensive agent in clinical studies on humans with certain forms of hypertension. However, BPP$_{9a}$ is not orally active as an anti-hypertensive agent. For a summary of the clinical aspects of BPP$_{9a}$ see Genest et al., supra, Chapter 6.3, pp. 163-4.

More recently, a series of proline derivatives has been found to be significantly more potent as inhibitors of angiotensin converting enzyme and as anti-hypertensive agents than BPP$_{9a}$. Of these proline derivatives, D-3-mercapto-2methylpropanoyl-L-proline has been reported to be the most effective, including being effective when administered orally. These proline and mercaptoproline derivatives and various pharmacological test results thereon are described in Cushman et al., "Design of New Anti-hypertensive Drugs: Potent and Specific Inhibitors of Angiotensin Converting Enzyme", Prog. in Cardio. Diseases, Vol. XXI, No. 3 (Nov./Dec., 1978), and in U.S. Pat. Nos. 4,046,889 and 4,105,776, both to Ondetti and Cushman.

DETAILED DESCRIPTION OF THE INVENTION

The generic description of the compounds of the invention is given above by Formulas I and II. A preferred group (IC) of compounds of Formula I are those in which $R_3$ is hydrogen or lower alkyl; and $R_4$ is —SH or

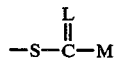

wherein

L is O, NR$_7$ or S (where R$_7$ is hydrogen or lower alkyl); and

M is R$_8$, OR$_8$, SR$_8$, or NR$_9$R$_{10}$ (where R$_8$ is hydrogen, lower alkyl, aryl or aralkyl; and R$_9$ and R$_{10}$ are, independently, hydrogen, lower alkyl, or aryl).

Another preferred group (ID) of compounds of Formula I are those in which R$_4$ is

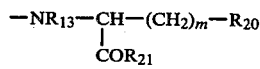

wherein:

m is 0, 1, 2 or 3;

R$_{13}$ is hydrogen or lower alkyl;

R$_{20}$ is hydrogen or aryl; and

R$_{21}$ is hydroxy or lower alkoxy.

Preferred compounds of the latter group (ID) are those in which R$_{13}$ is hydrogen; m is 2; R$_{20}$ is phenyl; Y is hydrogen; X is hydrogen; or R$_2$ is hydrogen. Particularly preferred compounds of this group (ID) are those in which m is 2, R$_{13}$ is hydrogen, R$_{20}$ is phenyl and R$_{21}$ is ethoxy, or hydroxy.

Further preferred compounds of Formula I include those in which Y is hydrogen, lower alkyl, or aryl; R$_1$ is hydrogen or lower alkyl; R$_4$ is thiol or arylcarbonylthio; n is 1; n is 1 and R$_2$ and R$_3$ are hydrogen; n is 0 and R$_2$ is hydrogen; and R$_5$ is hydroxy. Particularly preferred compounds of Formula I include those in which X is hydrogen; Y is hydrogen; R$_1$ is lower alkyl; R$_4$ is thiol or benzoylthio; n is 1, R$_1$ is lower alkyl, and R$_2$ and R$_3$ are hydrogen: and n is 0, R$_1$ is lower alkyl, and R$_2$ is hydrogen. A particularly preferred compound of Formula I is the compound of Example 40.

A preferred group of compounds of Formula II are those in which R$_3$ is hydrogen or lower alkyl. Further preferred compounds of Formula II include those in which Y is hydrogen, lower alkyl, or aryl; R$_1$ is hydrogen or lower alkyl; n is 1; n is 1 and R$_2$ and R$_3$ are hydrogen; and n is 0 and R$_2$ is hydrogen. Particularly preferred compounds of Formula II include those in which X is hydrogen; Y is hydrogen; R$_1$ is lower alkyl; n is 1, R$_1$ is lower alkyl, and R$_2$ and R$_3$ are hydrogen; and n is 0, R$_1$ is lower alkyl, and R$_2$ is hydrogen.

Where either Y or R$_3$ of Formula I or II is other than hydrogen, the carbon atom to which it is attached is an asymmetric carbon atom. Similarly, where R$_1$ and R$_2$ are different, the carbon atom to which they are attached is an asymmetric carbon atom. Additionally, the carbon atom designated 2 in Formula I and the carbon atom designated 11a in Formula IIa below and the carbon atom designated 10a in Formula IIb below are asymmetric.

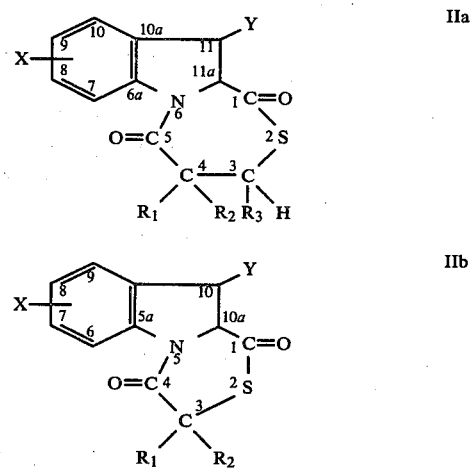

Where R$_4$ is —NR$_{13}$—CH(COR$_{21}$)(CH$_2$)$_m$—R$_{20}$, the carbon atom to which the —COR$_{21}$ group is attached is asymmetric. Thus, the compounds of the invention (including intermediate compounds) exist in stereoisomeric forms or in racemic mixtures thereof, all of which are within the scope of the invention.

The following compounds of Formula IIa are preferred: The compounds in which X, Y, R$_2$ and R$_3$ are hydrogen and R$_1$ is methyl, which is 11, 11a-dihydro-4-methyl-1H,3H-[1,4]thiazepino[4,3-a]indole; and the compound in which X, Y, R$_1$, R$_2$, and R$_3$ are hydrogen, which is 11,11a-dihydro-1H,3H[1,4]thiazepino[4,3-a]indole.

The following compounds of Formula IIb are preferred: The compound in which X, Y, and R$_2$ are hydrogen and R$_1$ is methyl, which is 10,10a-dihydro-3-methyl-1H-[1,4]thiazino[4,3-a]indole; and the compound in which X, Y, R$_1$, and R$_2$ are hydrogen, which is 10,10a-dihydro-1H-[1,4]thiazino[4,3-a]indole.

Also within the scope of the invention are the intermediate compounds of the formula:

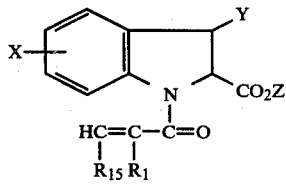

IV wherein:
R$_1$ is hydrogen, lower alkyl, aryl, or aralkyl;
R$_{15}$ is hydrogen or lower alkyl;
X is hydrogen, hydroxy, lower alkyl, lower alkoxy, or halogen;
Y is hydrogen, lower alkyl, or aryl; and
Z is a carboxylic acid protecting group;
or salts thereof.

Further within the scope of the invention are the intermediate compounds of the formula:

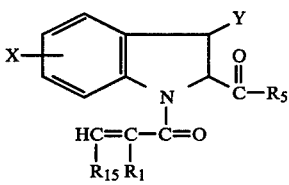

V wherein:
R$_1$ is hydrogen, lower alkyl, aryl, or aralkyl;
R$_{15}$ is hydrogen or lower alkyl;
R$_5$ is hydroxy, amino, or lower alkoxy;
X is hydrogen, hydroxy, lower alkyl, lower alkoxy, or halogen;
and
Y is hydrogen, lower alkyl, or aryl;
or salts thereof.

Further intermediates within the scope of the invention are those formed by the reaction of the reactants of the Formula VII with the starting materials III, which are represented by the formula:

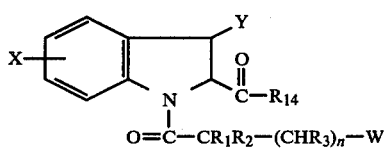

VIII wherein: n, X, Y, R$_1$, and R$_2$ are as previously defined; R$_3$ is hydrogen, lower alkyl, or aroyl; R$_{14}$ is R$_5$ or OZ (where R$_5$ and Z are as previously defined); and W is bromine, chlorine, or iodine or salts thereof. Those skilled in the art would also appreciate that W may be tosyloxy. R$_3$ is preferably hydrogen or lower alkyl.

Also included in the scope of the invention are the dimers (disulfides) of the compounds of Formula I in which R$_4$ is —SH. These compounds may be formed during the synthesis of the parent mercapto compound or may be made from the mercaptan by known methods.

The following flow diagram shows the general method of preparation of the compounds of the invention in which n is 1, R$_2$ is hydrogen, and R$_5$ is hydroxy.

Chart I

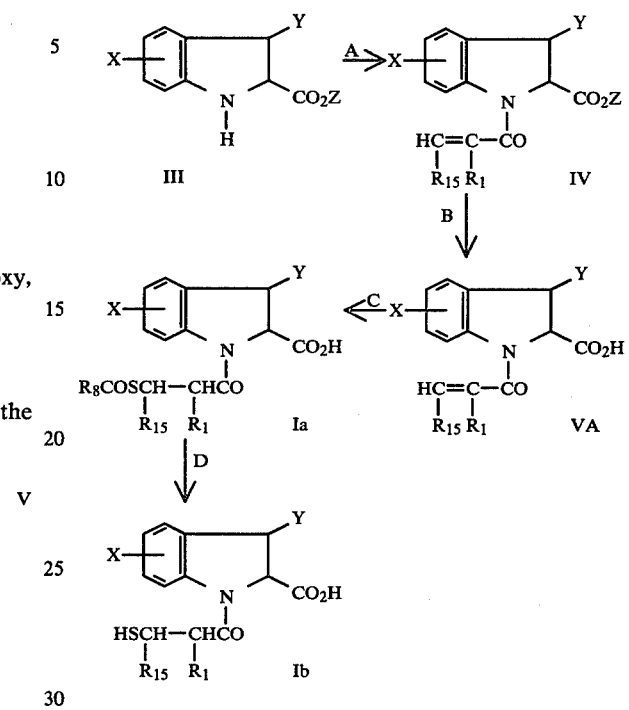

where X, Y, R$_1$, and R$_8$ are as defined above and Z is a carboxylic acid protecting group (including a lower alkyl group).

The preparation of the starting material (III) is described by Corey et al., J. Am. Chem. Soc., 92, 2476–2488 (1970). The desired X and Y substituents may be obtained on starting material III in a manner known to those skilled in the art.

The compound of the invention in which R$_5$ is an amino group may be obtained from the appropriately substituted 2,3-dihydro indole, 2-carboxylic acid or ester in a known manner. Where the starting material III then represents the amide or where the carboxylic acid protecting group (Z) is the desired lower alkyl group, the deprotection step (B) is not required. In such cases, R$_5$ is as desired in the end product.

In Step A of Chart I, the protected compound III is reacted with an acryloyl of the formula R$_{15}$HC=CR$_1$COR$_{16}$ (VI) wherein R$_1$ and R$_{15}$ are as defined above and COR$_{16}$ is an activated carboxyl group such as an acyl halide, an active ester, or mixed anhydride. The acyl halide group is preferred. This reaction is run in an inert organic solvent, such as ether or methylene chloride, in the presence of an acid scavenger, such as triethylamine, where an acid is formed during the reaction.

Alternately, in step A, a substituted alkyl acyl compound of the formula Br(CHR$_3$)$_n$CR$_1$R$_2$COR$_{16}$ (VII) wherein n, R$_1$, R$_2$, R$_3$, and R$_{16}$ are as previously defined, may be reacted with the starting material (III). In this procedure, the carboxylic acid group need not be protected, and step B may, therefore, be eliminated. Use of this route (i.e. utilizing reactant VII in step A) allows the preparation of all the compounds of the invention with respect to n, R$_1$, R$_2$, and R$_3$.

The carboxylic acid protecting group may be chosen from any known carboxylic acid protecting, for example, methyl, ethyl, and t-butyl esters and various amide groups. Various carboxylic acid protecting groups and their use as described in McOmie, ed., *Protective Groups in Organic Chemistry*, Chapter 5 (Plenum Press, 1973). An appropriate protective group should be selected on the basis that (1) the reagent by which it is introduced does not react with another part of the molecule; (2) the protective group does not interfere with subsequent reactions; and (3) the process by which it is removed does not effect other portions of the molecule.

In step B of Chart I, the carboxyl group is deprotected. For removal of an alkyl protecting group by hydrolysis treatment of the intermediate IV, first, with an aqueous dimethylsulfoxide-potassium hydroxide solution, followed by treatment with a dilute mineral acid, such as hydrochloric or sulfuric acid, is a convenient method. Other methods for deprotecting carboxylic acid groups are described in the literature, e.g. in *McOmie, Id.*

In step C, the thio group $R_4$ of the formula

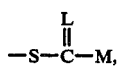

[wherein L is O, $NR_7$ or S (where $R_7$ is hydrogen or lower alkyl); and M is $R_8$, $OR_8$, $SR_8$, or $NR_9R_{10}$ (where $R_8$ is hydrogen, lower alkyl, aryl, or aralkyl; and $R_9$ and $R_{10}$ are, independently, hydrogen, lower alkyl, or aryl)] is coupled to the side-chain of the intermediate compounds (V) or to the intermediate compounds (VIII) resulting from the reaction of the starting material III with the reactant VII. The reactants utilized in step C to form the desired $R_4$ thio group (except where $R_4$ is —SH) are thio acids and thiols. These form a thioacyl or thio group by addition to the third carbon atom of the alkene side-chain (intermediates V) or by substitution for the bromine at the second or third carbon atom of the side-chain where the reactant VII was used. These reactions may take place in an inert organic solvent, such as methylene chloride, THF, or dioxone.

In order to form the compounds of the invention of Formula I in which $R_4$ is SH, a thiobenzyl compound is preferably formed in step C and removed by hydrolysis or ammonolysis in step D. Such ammonolyis may be accomplished by first treating the appropriate intermediate Ia with a methanolic ammonia solution and thereafter treating the resultant product with acid, such as HCl, to a pH of about 2.

In order to form the compounds of Formula II of the invention, a thioester cyclization of the mercapto compounds of Formula I is utilized. The formation of these thiolactones (i.e. the 1H,3H-[1,4]thiazepino[4,3-a]indoles and 1-H-[1,4]thiazino[4,3-a]indoles of Formula II) can be accomplished by a coupling reagent used widely in the peptide synthesis, such as dicyclohexylcarbodiimide (DCC) or N-ethyl-N'-(3-dimethylaminopropyl)-carbodiimide and related reagents. Example of such reagents are found in pp. 116-121 "Peptide Synthesis" (2nd Ed.) by M. Bodanszky, Y. S. Kalusner, and M. A. Ondetti, Wiley Interscience Publication, New York, 1976. The presence of small amounts of 4-dimethylaminopyridine is used to accelerate the reaction and increase the yield. The preferred reagent for the reaction is DCC in the presence of 4-dimethylaminopyridine used at room temperature for several hours in a methylene chloride medium. The same thioester cyclizations can be accomplished by treatment of the reactants with diethyl phosphocyanidate (DEPC) or diphenyl phosphorazidate (DPPA) in dimethylformamide in the presence of triethylamine [Yamada et al., J. Org. Chem., 39, 3302 (1974)], or by means of carbonyldiimidazole or carbonyl-di-1,2,4-triazole [Gais, Angew, Chem. Int. Edit. Engl., 16, 244 (1977)].

It will be appreciated that the various compounds of Formula Ia in which $R_4$ is

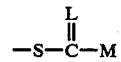

(where L and M are as defined above) are intermediates useful in the preparation the mercapto compounds of Formula Ib (where $R_4$ is —SH).

The step A alternate procedure may be used to produce the compounds in which $R_4$ is —APO($OR_{11}$)($OR_{12}$) (X). Thus, the compounds in which A is $NR_{13}$ may be made by first reacting an amine of the formula $H_2NR_{13}$ with the appropriate intermediate of Formula VIII to form a further intermediate of the formula N—[HN$R_{13}$(CH$R_3$)$_n$ —C$R_1R_2$—CO]—B (XI), where B is the desired 2,3-dihydro-1H-indole carboxylic acid (suitably protected) starting material. Intermediate XI may then be reacted with a chlorophosphate of the formula ClPO($OR_{11}$)($OR_{12}$)[where $R_{11}$ and $R_{12}$ are not hydrogen] (XII) to form the desired substituted amino phosphate end product. To form such end product where one or both of $R_{11}$ and $R_{12}$ is hydrogen requires appropriate selection of $R_{11}$ and $R_{12}$ to resist or be amenable to later catalytic hydrogenolysis. Where A is S in Formula X, the compounds of the invention may be made by reacting a mercaptophosphate of the formula HSPO($OR_{11}$)—($OR_{12}$) (XIII) directly with the appropriate intermediate of Formula VIII. In order to make those compounds of the invention in which A of Formula X is O, an intermediate of the Formula N—[HO—(CH$R_3$)$_n$—C$R_1R_2$—CO]—B (XIV), where the carboxylic acid group of B is protected, is formed from the appropriate intermediate of Formula VIII and, then, reacted with the appropriate chlorophosphate of Formula XII (with subsequent hydrogenolysis where necessary to obtain $R_{11}$ or $R_{12}$ as hydrogen). In order to make those compounds of the invention in which A is O and $R_{12}$ is H in Formula X, the appropriate intermediate of the Formula XIV may be reacted with an appropriate chlorophosphate of Formula XII in the presence of a base, such as pyridine or triethylamine. Again, where $R_{11}$ or $R_{12}$ is hydrogen is desired, this reaction will have to be followed by a catalytic hydrogenolysis. The reactants and reaction conditions utilized in forming the intermediates for and final products of those compounds of the invention in which $R_4$ is APO($OR_{11}$)($OR_{12}$) (X) are known to those skilled in the art. Further description of such methods of preparation may be found in European Pat. No. 9-183 to Merck & Company Inc., dated Apr. 2, 1980 (Derwent No. 25743C/15).

Compounds in which $R_4$ is —N$R_{13}$CH-(CO$R_{21}$)(CH$_2$)$_m$ $R_{20}$ may be prepared from intermediate XI by condensation with compounds of the formula BrCH(CO$R_{21}$)(CH$_2$)$_m$—$R_{20}$(XV) or $R_{21}$OC—CO—(CH$_2$)$_m$—$R_{20}$ (XVI). When XV is the reactant, conditions fostering nucleophic displacement may be used (for example, a polar solvent such as dimethyl formamide in the presence of a base, with or without the addition of catalytic quantities of potassium iodide). When XVI is the reactant, conditions fostering reductive alkylation may be employed. For example XI may be condensed with XVI in a solvent in the presence of hydrogen and a hydrogenation catalyst according to the general procedures described in W. E. Emerson, Organic Reactions IV, 174 (1948). Alternatively XI may be condensed reductively with XVI in an acidic buffered solvent with an alkali metal cyanoborohydride. General procedures for such condensations are described in R. F. Borch, M. D. Bernstein and H. D. Durst, J. Am. Chem. Soc., 93 2897 (1971). When $R_3$ is aroyl, the nucleophilic displacement type condensation is preferred.

A preferred method of making optically active 1-(S)-2,3-dihydro-1-[(S)-3-mercapto-2-methyl-1-oxopropyl]-1H-indole-2-carboxylic acid, the 3-benzoylthio precursor thereof, or the dicyclohexylamine salts of the latter comprises the following steps:

(a) Preparing l-3-benzoylthio-2-methyl propionyl chloride by admixing l-3-benzoylthio-2-methyl propionic acid with thionyl chloride in the presence of a catalytic amount of trialkylamine at room temperature and evaporating the volatile components in vacuo, (b) Condensing the said propionyl chloride with d,l-2,3-dihydro-1H-indole-2-carboxylic acid in a water immiscible solvent solution in the presence of two equivalents of trialkylamine at 0°–10° for 2–15 minutes and room temperature for 1–5 hours, (c) Isolating the crude condensation product by acidification, extraction, dehydration and evaporation, (d) Precipitating 1-(S)-2,3-dihydro-1-[(S)-3-benzoylthio-2-methyl-1-oxopropyl]-1H-indole-2-carboxylic acid dicyclohexylamine salt from an acetonitrile solution by the addition of dicyclohexylamine to an acetonitrile solution of the said crude condensation product.

(e) Optionally recrystallizing said dicyclohexylamine salt from a lower alkanol, (f) Regenerating the 1-(S)-2,3-dihydro-1-[(S)-3-benzoylthio-2-methyl-1-oxopropyl]-1H-indole-2-carboxylic acid by acidification with potassium hydrogen sulfate, extraction with a water immiscible solvent, dehydration and evaporation, and (g) Cleaving the benzoyl-thio bond by contacting, in an inert atmosphere, 1-(S)-2,3-dihydro-1-[(S)-3-benzoylthio-2-methyl-1-oxopropyl]-1H-indole carboxylic acid with an alkoxy lower alkyl amine, such as 2-methoxyethylamine, followed by acidification, extraction into a water immiscible solvent, dehydration and evaporation to give the desired 1-(S)-2,3-dihydro-1-[(S)-3-mercapto-2-methyl-1-oxopropyl]-1H-indole-2-carboxylic acid, which can be further purified by recrystallization from ethyl acetate-hexane.

The starting l-3-benzoylthio-2-methyl propionic acid may be obtained by a resolution of the racemic acid by formation of a salt with dehydroabietylamine followed by acidification. The starting d,l-2,3-dihydroindole-2-carboxylic acid is described in the literature.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful e.g., in isolating or purifying the product, as illustrated in the examples in the case of the dicyclohexylamine salt.

The compounds of Formula XI form acidic salts with various inorganic and organic acids, for example hydrochloric acid methanesulfonic acid (mesylate), and toluenesulfonic acid (tosylate). Such salts are also within the scope of the invention.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

The angiotensin converting enzyme (ACE) inhibitory property of the compounds is measured in vitro and in vivo. The in vitro assay utilizes rabbit lung extract and a specific tripeptide substrate, hippuryl-L-histidyl-L-leucine being preferred, and follows the method of Cushman et al., Biochem. Pharmacol., 20, 1637–1648 (1971).

The in vivo ACE inhibitory activity of the compounds is measured according to the procedure described in Rubin et al., J. Pharmacol. Exp. Ther., 204, 271–280 (1978), which utilizes the conscious normotensive tat as a subject. In this procedure, the jugular vein and carotid artery cannulae are placed in an etheranesthetized, normotensive, male, Sprague-Dawley rat for injection or oral dosage of compounds and direct recording of systemic arterial pressure, respectively. The blood pressure responses to I. V. injections of angiotensin I (500 ng/kg.), angiotensin II (100 ng/kg.) and bradykinin (10 μg/kg.) are recorded and compared with identical doses administered at various time intervals after oral dosing of a prospective angiotensin converting enzyme inhibitor. An angiotensin converting enzyme inhibitor would not be expected necessarily to lower arterial pressure in the normotensive rat, but would be expected to block angiotensin I pressor responses without grossly altering angiotensin II responses. Additionally, the vasodepressor response to bradykinin would be expected to be augmented since angiotensin converting enzyme is known to inactivate bradykinin normally.

When administered orally and intravenously according to this procedure, compounds of Formulas I and II (and disulfides) showed an ability to inhibit angiotensin converting enzyme at doses of 0.1–10 mg/kg.

The anti-hypertensive effect of the compounds of the invention is measured in the spontaneously hypertensive rat. In this procedure systolic pressure of male spontaneously hypertensive rats is measured by an indirect technique using the Decker Caudal Plethysmograph or other appropriate sensor. Groups usually consist of 4 or more rats. Drugs are usually administered orally. Pressures are usually read prior to drug administration and at 1.5, 4 and 24 hours thereafter. This schedule may be altered depending upon the behavior of the drug.

This procedure measures the hypotensive effect of the subject compounds in a hypertensive subject using a single dose and measuring the response over a 24 hour period. When administered orally according to this procedure, compounds of the invention produced a significant decrease in blood pressures in doses of 1–50 mg/kg. When used to treat hypertension in warm-blooded animals doses of less than 15 mg/kg./day would be utilized, and preferably doses of less than 5 mg/kg./day. Such effective treatment doses would generally be administered in long-term antihypertensive therapy. Angiotensin converting enzyme inhibitors when utilized as anti-hypertensive agents are most effective upon such extended administration and exhibit no significant side-effects when administered at moderate or low doses. As noted earlier, the compounds of the invention exhibit a hypotensive (depressor) response only when administered to hypertensive subjects and would not be expected to lower blood pressures significantly in normotensive subjects.

The compounds of Formulas I and I (and the disulfides of Formula I compounds) may be administered orally, intravenously, intraperitoneally, intramuscularly, or subcutaneously. Oral administration is preferred.

When employed to lower blood pressures in hypertensive subjects, the effective dosage of the compound being utilized for such treatment will vary according to the particular compound being employed, the severity and nature of condition being treated, and the particular subject being treated. Therapy should be initiated at lower doses (in mg/kg./day) in the effective ranges given above, the dosage thereafter being increased, if necessary, to produce the desired anti-hypertensive effect.

Further, when employed as anti-hypertensive agents or as angiotensin converting enzyme inhibitors, the compounds of the invention may be administered alone or in combination with pharmaceutically acceptable carriers. The proportion and nature of such carriers would be determined by the solubility and other chemical properties of the compound selected, the chosen route of administration, and standard pharmaceutical practice.

As previously noted, this invention also includes methods of treatment of hypertension in warm-blooded animals utilizing hypotensively effective amounts of the compounds of Formulas I and II (and the disulfides of the Formula I compounds in which $R_4$ is —SH). The generic and subgeneric aspects of this part of the invention encompass the same compounds and groups of compounds described above with respect to the compound portion of the invention.

The compounds of Formula XI are among the intermediates for which patent protection is sought. These compounds have the formula:

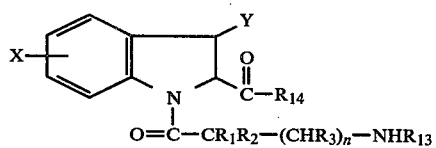

XI wherein X, Y, $R_1$, $R_2$, $R_3$, $R_{13}$, $R_{14}$ and n are as previously defined, or salts thereof. Preferred compounds of Formula XI are those in which n is O; $R_2$ is hydrogen; $R_{13}$ is hydrogen; X is hydrogen; Y is hydrogen; or $R_1$ is lower alkyl. Particularly preferred compounds of this aspect of the invention are those in which n is O, $R_2$ and $R_{13}$ are hydrogen and $R_1$ is lower alkyl.

The methods of making and using the compounds of the invention and the best mode of the invention are further illustrated in the following examples:

EXAMPLE 1

2,3-Dihydro-1-(2-methyl-1-oxo-2-propenyl)-1H-indole-2-carboxylic acid ethyl ester To a chilled and stirred mixture of 2,3-dihydroindole-2-carboxylic acid ethyl ester (4.78 g., 25.0 mmole), triethylamine (2.7 g., 26.7 mmole), and anhydrous ether (500 ml) was added dropwise methacryloyl chloride (2.9 g., 27.7 mmole) dissolved in a small amount of ether. After the completion of the addition, the ice bath was removed, and the reaction mixture was stirred for 4 hours. The precipitate which separated was removed by filtration, and the filter residue was washed with ether. The combined filtrate and washing were washed with water (two 700ml portions), then with saline, and dried over anhydrous magnesium sulfate. Evaporation of the solvent under reduced pressure on a rotary evaporator gave the product as an oil. The product was purified by preparative HPLC (Prep LC/System 500, Waters Associates), using a micro porasil column eluted with a mixture of hexane (95%) and ethyl acetate (5%). The crude oil may be used directly in the following reaction (Example 2).

EXAMPLE 2

2,3-Dihydro-1-(2-methyl-1-oxo-2-propenyl)-1H-indole-2-carboxylic acid

A mixture of 2,3-dihydro-1-(2-methyl-1-oxo-2-propenyl)-1H-indole-2-carboxylic acid ethyl ester (3.9 g., 15.0 mmole), 80% aqueous dimethylsulfoxide (90 ml.) and potassium hydroxide (86% pellets, 1.3 g., 19.9 mmole), was stirred under nitrogen atmosphere for 2 days at room temperature, then evaporated under reduced pressure on a rotary evaporator to give an oily residue. The residue was dissolved in water (any insoluble material was removed by filtration), and the aqueous solution was made acidic by careful addition of dilute hydrochloric acid, whereby an oil separated. The oily product was extracted with ether, and the ether extract was washed with water (3 times), then with saline. The ether solution was dried over anhydrous magnesium sulfate, and evaporated under reduced pressure to give an oily product. The oil was dissolved in dry acetonitrile, and dicyclohexylamine was added dropwise until the pH of the solution reached approximately 8.5. A crystalline precipitate was filtered. The mixture was allowed to stand overnight at room temperature, and the precipitate was collected on a filter, and the filter residue was washed with ether several times to give 3.46 g. of 2,3-dihydro-1-(2-methyl-1-oxo-2-propenyl)-1H-indole-2-carboxylic acid dicyclohexylamine salt (m.p. 185°–190°). Recrystallization from 2-propanol gave 3.1 g. (50.0%) of the title product as the dicyclohexylamine salt (m.p. 193°–195°) [m.p. means melting point in degrees centigrade, uncorrected.]

Analysis for: $C_{25}H_{35}N_3O_3.\frac{1}{4}H_2O$: Calculated: C, 72.16; H, 8.60; N, 6.73: Found: C, 72.05; H, 8.83; N, 6.64.

The salt was partitioned between 5% aqueous potassium bisulfate solution (50 ml.) and ethyl acetate (3 times), and the ethyl acetate extract was washed with water, then dried over anhydrous magnesium sulfate. Evaporation of the ethyl acetate solution under reduced pressure on a rotary evaporator afforded 1.8 g. of free 2,3-dihydro-1-(2-methyl-1-Oxo-2-propenyl)-1H-indole- 2-carboxylic acid in resinous form which solidified on standing. The solid was dissolved in ether, and the ether solution was evaporated in open air, whereby a precipitate separated. The mixture was chilled in ice, and the precipitate was collected on a filter and washed with ether. The product melted at 138°–140°.

Analysis for: $C_{13}H_{13}NO_3$: Calculated: C, 67.52; H, 5.67; N, 6.06: Found: C, 67.15; H, 5.75; N, 5.76.

EXAMPLE 3

1-(3-Benzoylthio-2-methyl-1-oxopropyl)-2,3-dihydro-1H-indole-2-carboxylic Acid

A. Thiobenzoic acid (95%, 0.75 g., 5.2 mmole) dissolved in dry methylene chloride (ca. 3 ml.) was added to a solution of 2,3-dihydro-1-(2-methyl-1-oxo-2-propenyl)-1H-indole-2-carboxylic acid (1.2 g., 5.2 mmole) in dry methylene chloride (25 ml.) chilled in an ice bath. The ice bath was removed, and the reaction was stirred at room temperature for 0.5 hr. The reaction mixture was then immersed in an oil maintaining the temperature of 85±5° for 3 hrs., and evaporated under reduced pressure using a rotary evaporator to give a resinous residue. Addition of a small amount of ethanol to the residue caused a partial solidification of the residue. The solid material was separated by filtration, and recrystallized from ethanol to give 0.4 g. (21%) of a product which melted at 187°–188°. Analytical sample which was obtained by recrystallization from ethanol melted at 188°–190°. Thin-layer chromatography carried out on a Merck silica gel plate using a mixture of methylene chloride (8), ethanol (2), triethylamine (1), and toluene (1) showed one spot with $R_f$ 0.7.

Analysis for: $C_{20}H_{19}NO_4S$: Calculated: C, 65.02; H, 5.18; N, 3.79; Found: C, 64.63; H, 5.27; N, 3.69.

B. The mother liquors from the above recrystallizations were evaporated to give a resinous material. The residue was dissolved in ether, and the ether solution was evaporated under a slow nitrogen stream to cause a crystalline material to be deposited. The crystalline deposit was filtered and recrystallization from ether to give 0.5 g. (25%) of the product containing a ¼ mole of ether solvate, m.p. 116°–117°. This product is the racemic diastereoisomer of the material that melted at 188°–190° (Example 3A). Thin-layer chromatography carried out on a Merck silica gel plate using a mixture of methylene chloride (8), ethanol (2), triethylamine (1), and toluene (1) as a developing solution showed one spot with $R_f$ 0.6.

Analysis for: $C_{20}H_{19}NO_4S \cdot \frac{1}{4}Et_2O$: Calculated: C, 65.01; H, 5.59; N, 3.61: Found: C, 64.71; H, 5.51; N, 3.32.

EXAMPLE 1

2,3-Dihydro-1-(3-mercapto-2-methyl-1-oxopropyl)-1H-indole-2-carboxylic acid

A mixture of 1-[3-(benzoylthio)-2-methyl-1-oxopropyl]-2,3-dihydro-1H-indole-2-carboxylic acid (Example 3A, m.p. 188°–190°) (0.6 g., 1.6 mmole) and methanolic ammonia (5.5 N solution, 9 ml.) was stirred at room temperature for 2.5 hours, then evaporated under reduced pressure on a rotary evaporator to give a resinous material. The residue was dissolved in water, and then the aqueous solution was washed with ether three times. The aqueous layer was made acidic by dropwise addition of dilute hydrochloric acid until pH of the solution reached approximately 2 (by a pH paper). The oil thus separated was extracted with ethyl acetate (twice) and the ethyl acetate extract was washed with water, then with saline, and dried over anhydrous magnesium sulfate. Evaporation of ethyl acetate on a rotary evaporator under reduced pressure, then in vacuo gave an oil. The residue was dissolved in dry acetonitrile, and dicyclohexylamine was added dropwise until pH of the solution reached ca. 8.5. The resulting mixture was kept at room temperature for 2 hours, then in a cold room for ca. 0.5 hour. The precipitate that separated was collected on a filter, and washed with acetonitrile to give 2,3-dihydro-1-(3-mercapto-2-methyl-1-oxopropyl)-1H-indole-2-carboxylic acid, dicyclohexylamine salt (yield, 0.63 g., m.p. 203°–205°). The melting point of a mixture of this salt and the DCHA salt of Example 5 was depressed.

Analysis for: $C_{25}H_{38}N_2O_3S$: Calculated: C, 67.22; H, 8.58; N, 6.27: Found: C, 66.88; H, 8.33; N, 6.29.

The salt (0.6 g.) was added to 3% aqueous potassium bisulfate solution (10 ml.), and was shaken vigorously. The free acid thus formed was extracted with ethyl acetate (17 ml. in 2 times). The extract was washed successively with water and saline, and dried over anhydrous magnesium sulfate. Evaporation of ethyl acetate on a rotary evaporator under reduced pressure afforded a glassy residue. The residue was dissolved in a small amount of ether and the ether solution was added dropwise, under vigorous stirring, to a large volume of hexanes chilled in ice. The fluffy white precipitate that separated was collected on a filter, and dried in vacuo, giving 0.12 g. of 2,3-dihydro-1-(3-mercapto-2-methyl-1-oxopropyl)-1H-indole-2-carboxylic acid.

Analysis for: $C_{13}H_{15}NO_3S$: Calculated: C, 58.84; H, 5.70; N, 5.28: Found: C, 59.24; H, 5.95; N, 5.16.

EXAMPLE 5

2,3-Dihydro-1-(3-mercapto-2-methyl-1-oxopropyl)-1H-indole-2-carboxylic acid

A mixture of 1-[3-(benzoylthio)-2-methyl-1-oxopropyl]-2,3-dihydro-1H-indole-2-carboxylic (Example 3B, m.p. 116°–117°) isolated with a ¼ mole of ether from the mother liquor of Example 3A (1.0 g., 2.6 mmole) and methanolic ammonia (5.5 N solution, 100 ml.) was stirred at room temperature for 2.5 hours then evaporated under reduced pressure on a rotary evaporator to give a resinous material. The residue was dissolved in water (20 ml.), and the aqueous solution was made alkaline by addition of five drops of 2 N aqueous sodium hydroxide solution. The alkaline solution was washed with ether three times, then was made acidic by addition of dilute hydrochloric acid. The oily product thus separated was extracted with ether (110 ml. in 3 times). The ether extract was washed with water, then with saline, and dried over anhydrous magnesium sulfate. Evaporation of ether under reduced pressure on a rotary evaporator gave a resinous material which was dissolved in acetonitrile (15 ml.). The dropwise addition of dicyclohexylamine (ca. 0.65 g.) to the acetonitrile solution under stirring until pH of the solution reached 8.5 (by a pH paper), and subsequent cooling in a cold room overnight caused separation of 2,3-dihydro-1-(3-mercapto-2-methyl-1-oxopropyl)-1H-indole-2-carboxylic acid, dicyclohexylamine salt as a precipitate. The precipitate was collected on a filter and washed with acetonitrile to give 1.0 g. of material which melted at 190°–193°. Recrystallization from 2-propanol improved the melting point to 193°–195°. The melting point of a mixture of this salt and the DCHA salt of Example 1 compound was depressed.

Analysis for: $C_{25}H_{38}N_2O_3S$: Calculated: C, 67.22; H, 8.58; H, 6.27: Found: C, 67.09; H, 8.58; N, 6.33.

The salt (0.744 g.) was added to 5% aqueous potassium bisulfate solution (10 ml.), and was shaken vigorously. The free acid thus formed was extracted with ethyl acetate (25 ml. in 2 times). The extract was washed successively with water and saline, and dried over anhydrous magnesium sulfate. Evaporation of ethyl acetate on a rotary evaporator under reduced pressure afforded a glassy residue. The residue was dissolved in 25 ml. of ether, and the ether solution was added dropwise under vigorous stirring to a large volume of hexanes (300 ml.) chilled in ice. The white solid precipitate which separated was collected on a filter, and washed with hexanes, giving 280 mg. of the title compound. The mass spectrum obtained using a AEI MS 902-Kratos DS 50 S spectrometer showed peaks at m/e 265 (M+), 163 and 118.

Analysis for: $C_{13}H_{15}NO_5S$: Calculated: C, 58.64; H, 5.70; N, 5.28: Found: C, 58.61; H, 5.62; N, 4.88.

EXAMPLE 6

2,3-Dihydro-1-(1-oxo-2-propenyl)-1H-indole-2-carboxylic acid ethyl ester

To a chilled and stirred mixture of 2,3-dihydroindole-2-carboxylic acid ethyl ester (14.34 g.), triethylamine (7.65 g.) and anhydrous ether (600 ml.) was added dropwise acryloyl chloride (7.1 g.) dissolved in a small amount of ether. The ice bath was removed, and the reaction mixture was stirred at room temperature for 4 hours. The reaction mixture was chilled in ice, then a precipitate was removed by filtration. The filter residue was washed with ether. The combined filtrate and washing were washed with water, then with saline, and dried over anhydrous magnesium sulfate. Evaporation of the solvent under reduced pressure on a rotary evaporator gave the titled compound (14.4 g.) as an oil.

EXAMPLE 7

2,3-Dihydro-1-(1-oxo-2-propenyl)-1H-indole-2-carboxylic acid

A mixture of 2,3-dihydro-1-(1-oxo-2-propenyl)-1H-indole-2-carboxylic acid ethyl ester (14.4 g.), 80% aqueous dimethylsulfoxide (200 ml.) and potassium hydroxide (86% pellets, 5.83 g.) was stirred under nitrogen atmosphere for 2.5 days at room temperature, then evaporated under reduced pressure on a rotary evaporator to give an oily residue. The residue was dissolved in water with the aide of a small amount of dilute sodium hydroxide solution. The aqueous solution was washed with ether twice, then made acidic by addition of dilute hydrochloric acid to pH ca. 2. The oil thus separated was extracted with ether three times. The combined ether extract was washed with water, then with saline, and dried over anhydrous magnesium sulfate. Evaporation of the ether on a rotary evaporator under reduced pressure gave a solid residue which melted at 158°–160°, and weighed 9.2 g. Recrystallization from ethyl acetate improved the melting point to 167°–169°.

Analysis for: $C_{12}H_{11}NO_3$: Calculated: C, 66.35; H, 5.11; N, 6.45: Found: C, 66.16; H, 5.10; N, 6.33.

EXAMPLE 8

1-[3-(Benzoylthio)-1-oxo-propyl]-2,3-dihydro-1H-indole-2-carboxylic acid

To a stirring mixture of 2,3-dihydro-1-(1-oxo-2-propenyl)-1H-indole-2-carboxylic acid (6.52 g.) and methylene chloride (160 ml.) was added dropwise thiobenzoic acid (95%, 4.36 g.) dissolved in a small amount of methylene chloride. During the addition, the reaction mixture was chilled in ice. The ice bath was removed in 10 minutes after the completion of the addition, but the stirring was continued for 1 hour. The reaction mixture was then immersed in an oil bath maintained at 80° for 2.5 hours. The reaction mixture was concentrated on a rotary evaporator under reduced pressure to ca. 30 ml., and kept in a refrigerator for 1 day. A precipitate was collected on a filter and washed with methylene chloride to give the titled compound which melted at 173°–175°, and weighed 11.0 g.

Analysis for: $C_{19}H_{17}NO_4S$: Calculated: C, 64.21; H, 4.82; N, 3.94: Found: C, 64.38; H, 4.93; N, 3.96.

EXAMPLE 9

2,3-Dihydro-1-(3-mercapto-1-oxopropyl)-1H-indole-2-carboxylic acid

A mixture of 1-[3-(benzoylthio)-1-oxopropyl]-2,3-dihydro-1H-indole-2-carboxylic acid (3.0 g.) and methanolic ammonia (5.5 N solution, 45 ml.) was stirred at room temperature for 2.5 hours, then evaporated under reduced pressure on a rotary evaporator to give a resinous material. The residue was dissolved in water, and the aqueous solution was washed with ethyl acetate three times. The aqueous phase was acidified to pH ca. 2 by dropwise addition of dilute hydrochloric acid, whereby an oil separated. The oil was extracted with ethyl acetate (two times). The combined extract was washed with water, then with saline, and dried over anhydrous sodium sulfate. The ethyl acetate was evaporated on a rotary evaporator under reduced pressure to give an oily residue which was placed under high vacuum to give a solid material. The crude product was dissolved in a small amount of warm ethyl acetate with warming on a steam bath (there was some insoluble solid material which was removed by filtration). The ethyl acetate solution was kept under mild nitrogen stream until a precipitate started to separate. The mixture was chilled in ice, then kept in a refrigerator. The precipitate was collected on a filter and washed with acetonitrile to give 1,1'-dithiobis[3-oxo-1,3-propanediyl]bis[2,3-dihydro-1H-indole-2-carboxylic acid], m.p. 213°–216°.

Analysis for: $C_{24}H_{24}N_2O_6S_2$: Calculated: C, 57.58; H, 4.83; N, 5.60: Found: C, 57.56; H, 4.96; N, 5.43.

The mother liquor and washings were combined, and evaporated on a rotary evaporator under reduced pressure to dryness. The residue was dissolved in acetonitrile with warming on a steam bath. Dicyclohexylamine was added to the solution until pH of the solution reached ca. 8.0 (by a pH paper). The dicyclohexylamine salt thus formed was collected on a filter, and recrystallized from ethanol. The salt melted at 203°–205°.

Analysis for: $C_{12}H_{13}NO_3S$: Calculated: C, 66.63; H, 8.59; N, 6.18: Found: C, 66.35; H, 8.14; N, 6.06.

The salt was shaken with 5% aqueous potassium bisulfate solution (70 ml.), and the free acid thus separated was extracted with ethyl acetate (70 ml. in two times). The combined extract was washed with water, then with saline, and dried over anhydrous sodium sulfate. Evaporation of ethyl acetate on a rotary evaporation under reduced pressure gave a solid residue which was recrystallized from ethyl acetate. The titled compound melted at 146°-148° dec.

Analysis for: $C_{12}H_{13}NO_3S$: Calculated: C, 57.35; H, 5.21; N, 5.57: Found: C, 57.39; H, 5.27; N, 5.37.

EXAMPLE 10

Resolution of
d,l-2,5-dihydro-1-(2-methyl-1-oxo-2-propenyl)-1H-indole-2-carboxylic acid into
d-2,3-dihydro-1-(2-methyl-1-oxo-2-propenyl)-1H-indole-2-carboxylic acid and
l-2,3-dihydro-1-(2-methyl-1-oxo-2-propenyl)-1H-indole-2-carboxylic acid A. To a hot vigorously stirred methanolic solution of d,l-2,3-dihydro-1-(2-methyl-1-oxo-2-propenyl)-1H-indole-2-carboxylic acid of Example 2 (29 g. in 300 ml. of methanol) was added slowly a warm methanolic solution of dehydroabietylamine(DHAA, 18.9 g. in 60 ml. of methanol). The stirring was continued for additional 5 minutes, then allowed to set at room temperature for 10 minutes. The mixture was reheated to boiling, and to the hot, vigorously stirred solution was added hot water (240 ml.). The resulting mixture was placed in a refrigerator overnight. The white precipitate that separated was collected on a filter, and washed with cold aqueous methanol solution[methanol (300 ml.)/water (250 ml.)] 5 times, giving d-2,3-dihydro-1-(2-methyl-1-oxopropenyl)-1H-indole-2-carboxylic acid, DHAA salt (27.9 g.), m.p. 207°-209° C. The combined filtrate and washings were set aside for isolation of l-2,3-dihydro-1-(2-methyl-1-oxo-2-propenyl)-1H -indole-2-carboxylic acid. Recrystallization of the DHAA salt (filter residue) from methanol improved the m.p. to 218°-219° C., $\alpha]_D^{25}=84.24$ (c=0.985%, EtOH).

Analysis for: $C_{13}H_{13}NO_3.C_{20}H_{31}N$: Calculated: C, 76.70; H, 8.58; N, 5.42: Found: C, 76.15; H, 8.53; N, 5.19.

The salt was pulverized with a mortar and pestle and partitioned between 1 N aqueous sodium hydroxide solution and ether. The aqueous layer was collected, and washed with ether twice, and acidified with dilute hydrochloric acid. The free acid that separated was extracted with ether 3 times. The combined extracts were washed with water, then with saline twice, and dried over anhydrous sodium sulfate. Evaporation of ether under reduced pressure gave a solid residue which was recrystallized from ether, giving d-2,3-dihydro-1-(2-methyl-1-oxo-2-propenyl)-1H-indole-2-carboxylic acid, m.p. 148°-150° C., $\alpha]_D^{23.3}=+133.45$ (c=1.11%, EtOH).

Analysis for: $C_{13}H_{13}NO_3$ (231.24): Calculated: C, 67.52; H, 5.67; N, 6.06: Found: C, 67.36; H, 5.71; N, 5.96.

B. The original combined filtrate and washings (aqueous methanol solution) were evaporated carefully on a rotary evaporator under reduced pressure to ca. 120 ml., then placed in a refrigerator overnight. The solid material which separated was collected on a filter, washed with cold water, and dried in vacuo. The dried filter residue (18.7 g., m.p. 130°-134° C.) was pulverized with a mortar and pestle, and dissolved in warm anhydrous ether (600 ml.). The supernatant liquid was filtered through a course folded filter paper. The insoluble residue was warmed with anhydrous ether (ca. 300 ml.), and supernatant liquid was combined with the original filtrate filtering through the same filter paper. This ether extraction was repeated two additional times (ca. 200 ml., and ca. 100 ml. in each time). The combined ether extracts were allowed to set at room temperature overnight. A small amount of fluffy material that deposited was removed by filtration, and the filtrate was concentrated on a rotary evaporator to a slurry. The residue was chilled, and filtered on a suction filter. The filter residue was washed with cold ether to give crude l-2,3-dihydro-1-(2-methyl-1-oxo-2-prophenyl)-1H-indole-2-carboxylic acid (12.3 g., m.p. 140°-143° C.). The crude product was dissolved in anhydrous ether (ca. 600 ml. in 3 portions), filtered, and the filtrate was concentrated to ca. 300 ml. The concentrated solution was refiltered, and the filtrate was diluted with hexane until it became cloudy. The mixture was stored in a freezer overnight. The precipitate that separated was collected on a filter, and washed with cold ether, giving the l-isomer (10 g.) with m.p. 147°-148° C. and $\alpha]_D^{25.5}=-122.5$ (c=0.835, EtOH). Further purification by recrystallization in the above fashion gave l-2,3-dihydro-1-(2-methyl-1-oxo-2-propenyl)-1H-indole-2-carboxylic acid with m.p. 152°-154° C. and $\alpha]_D^{25}=135.9$ (c=0.935, EtOH).

Analysis for: $C_{13}H_{13}NO_3$: Calculated: C, 67.52; H, 5.67; N, 6.06: Found: C, 67.33; H, 5.68; N, 6.04.

EXAMPLE 11 l-(S)-1-[(S)-3-(benzoylthio)-2-methyl-1-oxopropyl]-2,3-dihydro-1H-indole-2-carboxylic acid, dicyclohexylamine salt To a stirred solution of thiobenzoic acid (95% purity; 8.0 g.) in acetone (450 ml.) under nitrogen atmosphere was added 4-dimethylaminopyridine (0.61 g.) The resulting mixture was stirred for 5 minutes and then l-2,3-dihydro-1-(2-methyl-1-oxo-2-propenyl)-1H-indole-2-carboxylic acid (11.56 g., Example 10 B) was added. The resulting mixture was heated under reflux for 6 hours. Evaporation of the acetone in vacuo gave a resinous residue which was dissolved in methylene chloride. The methylene chloride solution was washed twice with cold 1 N hydrochloric acid, twice with saline, and dried over anhydrous magnesium sulfate. Evaporation of methylene chloride solution on a rotary evaporator under reduced pressure gave a foamy resinous material. The residue was dissolved in dry acetonitrile (250 ml.) and the solution was chilled in ice. Dicyclohexylamine (9.2 g.) was added slowly to the cold acetonitrile solution with agitation, and the resulting mixture was chilled for 2 hours. The precipitate was collected on a filter, and washed with acetonitrile 5 times, then with ethanol repeatedly, giving crude l-(S)-1-[(S)-3-(benzoylthio)-2-methyl-1-oxo-propyl]-2,3-dihydro-1H-indole-2-carboxylic acid, dicyclohexylamine salt (17.76 g., m.p. 193°-198° C.). (The filtrate and washings were combined, and set aside for isolation of d-(S)-1-[(R)-3-(benzoylthio)-2-methyl-1-oxopropyl]-2,3-dihydro-1H-indole-2-carboxylic acid, dicyclohexylamine salt.) Recrystallization of the crude product from ethanol improved the m.p. to 219°-221° C. (yield, 12.13 g.), $\alpha]_D^{23}=-69.16$ (c=1.035%, EtOH). The sample which melted at 222°-224° showed $\alpha]_D^{22.5}=76.6$ (c=1.135%, EtOH).

Analysis for: $C_{20}H_{19}NO_4S.C_{12}H_{23}N$: Calculated: C, 69.78; H, 7.69; N, 5.09: Found: C, 69.53; H, 7.73; N, 5.14.

EXAMPLE 12 d-(S)-1-[(R)-3-(benzoylthio)-2-methyl-1-oxopropyl]-2,3-dihydro-1H-indole-2-carboxylic acid, dicyclohexylamine salt A mixture of l-2,3-dihydro-1-(2-methyl-1-oxo-2-propenyl)-1H-indole-2-carboxylic acid (5.78 g. of Example 10 B), thiobenzoic acid (95% purity, 5 g.) and methylene chloride (70 ml.) was refluxed under nitrogen atmosphere for 8.5 hours, then evaporated on a rotary evaporator under reduced pressure to give a resinous residue. The residue was dissolved in acetonitrile (50 ml.) and ca. 5.0 g. of dicyclohexylamine was added dropwise to the acetonitrile solution (pH of the mixture was ca 6.5 when tested by a wet pH paper). The resulting mixture was chilled in a refrigerator for 1.5 hours. (The precipitate was collected on a filter, and the filter residue was washed with acetonitrile, giving crude l-(S)-1-(S)-3-(benzoylthio)-2-methyl-1-oxopropyl]-2,3-dihydro-1H-indole-2-carboxylic acid, dicyclohexylamine salt as in Example 11.) The combined filtrate and washings were placed in a hood overnight, and chilled in ice. The precipitate that separated was removed by filtration, and the mother liquor was treated with an additional amount of dicyclohexylamine until the pH of the solution reached 8. The resulting solution was concentrated by allowing to evaporate in a hood overnight, then chilled in ice. The precipitate that separated was collected on a filter and washed with acetonitrile, giving crude d-(S)-[(R)-3-(benzoylthio)-2-methyl-1-oxopropyl]-2,3-dihydro-1H-indole-2-carboxylic acid, dicyclohexylamine salt (7.39 g., m.p. 127°-130°). Purification by recrystallization from acetonitrile improved the m.p. 132°-134°, $[\alpha]_D^{22.5} = +26.00$ (c=1.04%, EtOH).

Analysis for: $C_{20}H_{19}NO_4S.C_{12}H_{23}N$: Calculated: C, 69.78; H, 7.69; N, 5.09: Found: C, 69.83; H, 7.64; N, 5.01.

EXAMPLE 15 d-(R)-1-[(R)-3-(benzoylthio)-2-methyl-1-oxopropyl]-2,3-dihydro-1H-indole-2-carboxylic acid, dicyclohexylamine salt A mixture of d-2,3-dihydro-1-(2-methyl-1-oxo-2-propenyl)-1H-indole-2-carboxylic acid (2.31 g., Example 10 A) thiobenzoic acid (95% purity, 1.60 g.), and methylene chloride (50 ml.) was heated under reflux for 6 hours, then evaporated on a rotary evaporator under reduced pressure to give a resinous material. The residue was dissolved in acetonitrile and chilled. The cold solution was treated with ca 2.0 g. of dicyclohexylamine until pH of the mixture became approximately 8.5. The resulting mixture was chilled in ice for 1.5 hours, and a precipitate was collected on a filter and washed with acetonitrile, giving crude d-(R)-1-[(R)-3-(benzoylthio)-2-methyl-1-oxopropyl]-2,3-dihydro-1H-indole-2-carboxylic acid, dicyclohexylamine salt (2.65 g., m.p. 201°-204°). (The filtrate and washings were combined, and set aside for isolation of l-(R)-1-[(S)-3-(benzoylthio)-2-methyl-1-oxopropyl]-2,3-dihydro-1H-indole-2-carboxylic acid, dicyclohexylamine salt.) Recrystallization of the crude product from ethanol improved the m.p. to 219°-221° (yield 1.4 g.). Another recrystallization from ethanol gave an analytical sample, m.p. 222°-224°, $[\alpha]_D^{25.5} = +70.59$ (c=0.975%, EtOH).

Analysis for: $C_{20}H_{19}NO_4S.C_{12}H_{23}N$: Calculated: C, 69.78; H, 7.69; N, 5.09: Found: C, 69.52; H, 7.64; N, 5.09.

EXAMPLE 14

1-(R)-1-[(S)-3-(benzoylthio)-2-methyl-1-oxopropyl]-2,3-dihydro-1H-indole-2-carboxylic acid, dicyclohexylamine After the combined acetonitrile filtrate and washings from Example 13 were allowed to set at room temperature for several days, the precipitate that separated was collected on a filter and was washed with acetonitrile, giving crude l-(R)-1-[(S)-3-(benzoylthio)-2-methyl-1-oxopropyl]-2,3-dihydro-1H-indole-2-carboxylic acid, dicyclohexylamine salt (0.94 g., m.p. 131°-133°).

Recrystallization from acetonitrile, then from ethyl acetate improved the m.p. to 133°-135°, $[\alpha]_D^{24.5} = -20.18$ (c=1.02%, EtOH).

Analysis for: $C_{20}H_{19}NO_4S.C_{12}H_{23}N$: Calculated: C, 69.78; H, 7.69; N, 5.09: Found: C, 69.96; H, 7.63; N, 5.02.

EXAMPLE 15 l-(S)-1-[(S)-3-(benzoylthio)-2-methyl-1-oxopropyl]-2,3-dihydro-1H-indole-2-carboxylic acid Powdered l-(S)-1-[(S)-3-(benzoylthio)-2-methyl-1-oxopropyl]-2,3-dihydro-1H-indole-2-carboxylic acid, dicyclohexylamine salt*(2.0 g.) was shaken vigorously with a mixture of 5% aqueous potassium hydrogensulfate (50 ml.) and ethyl acetate (45 ml.) in a separatory funnel, and the ethyl acetate layer was separated. The aqueous layer was extracted two additional times with ethyl acetate (20 ml. and 10 ml.) The combined ethyl acetate extracts were washed with water, then with saline, and dried over anhydrous sodium sulfate. Evaporation of the solvent on a rotary evaporator under reduced pressure gave an oily residue which solidified on standing. Recrystallization from ether and hexanes gave l-(S)-1-[(S)-3-(benzoylthio)-2-methyl-1-oxopropyl]-2,3-dihydro-1H-indole-2-carboxylic acid, (1.25 g.), m.p. 144°-146°, $[\alpha]_D^{25} = -183.6$ (c=1.07% EtOH). [* of Example 11]

Analysis for: $C_{20}H_{19}NO_4S$: Calculated: C, 65.02; H, 5.18; N, 3.79: Found: C, 65.03; H, 5.39; N, 3.78.

EXAMPLE 16 d-(S)-1-[(R)-3-(benzoylthio)-2-methyl-1-oxopropyl]-2,3-dihydro-1H-indole-2-carboxylic acid The title compound was obtained in resinous form from the corresponding dicyclohexylamine salt of Example 12 (2.5 g.) by the treatment with 5% aqueous potassium hydrogen sulfate solution as described in Example 15. $[\alpha]_D^{22.5} = +65.29$ (c=1.145%, EtOH).

Analysis for: $C_{20}H_{19}NO_4S$: Calculated: C, 65.02; H, 5.18; N, 3.79: Found: C, 64.90; H, 5.30; N, 3.51.

EXAMPLE 17 d-(R)-1-[(R)-3-(benzoylthio)-2-methyl-1-oxopropyl]-2,3-dihydro-1H-indole-2-carboxylic acid The title compound (0.38 g.) was obtained from the corresponding dicyclohexylamine salt of Example 13 (0.7 g.) by the treatment with 5% aqueous potassium hydrogen sulfate solution as described in Example 15, m.p. 143°-145°, $[\alpha]_D^{25.5} = +179.33$ (c=1.04%, EtOH).

Analysis for: $C_{20}H_{19}NO_4S$: Calculated: C, 65.02; H, 5.18; N, 3.79: Found: C, 64.92; H, 5.32; N. 3.79.

EXAMPLE 18

1-(R)-1-[(S)-3-(benzoylthio)-2-methyl-1-oxopropyl]-2,3-dihydro-1H-indole-2-carboxylic acid The title compound was obtained from the corresponding dicyclohexylamine salt of Example 14 by the treatment with 5% aqueous potassium hydrogen sulfate solution as described in Example 15.

EXAMPLE 19 d,l-1-[3-(Acethythio)-2-methyl-1-oxopropyl]-2,3-dihydro-1H-indole-2-carboxylic acid, dicyclohexylamine salt A mixture of 2,3-dihydro-1-(2-methyl-1-oxopropenyl)-1H-indole-2-carboxylic acid (6.94 g.), thioacetic acid (95% purity, 3.9 g.), and methylene chloride (90 ml.) was heated under reflux for 5.5 hours, then evaporated on a rotary evaporator under reduced pressure to give a resinous residue. The residue was dissolved in acetonitrile (70 ml.) and chilled in ice. Dicyclohexylamine (ca. 5 g.) was added dropwise to the cold acetonitrile solution until pH of the solution reached about 8. The resulting mixture was allowed to set at room temperature for 2 hours, then in a refrigerator for 1 hour. A precipitate was collected on a filter and washed with acetonitrile 4 times. (The filtrate and washings were combined, and stored for isolation of the diastereoisomer of the product which precipitated first.) Several recrystallizations of the residue from ethanol gave d,l-1-[3-(acetylthio)-2-methyl-1-oxopropyl]-2,3-dihydro-1H-indole-2-carboxylic acid, dicyclohexylamine salt (2.65 g.) with m.p. 218°–220°.

Analysis for: $C_{15}H_{17}NO_4S.C_{12}H_{23}N$: Calculated: C, 66.36; H, 8.25; N, 5.73: Found: C, 66.60; H, 8.08; N, 5.62.

The combined acetonitrile filtrate and washings were concentrated to ca. 30 ml., then allowed to set at room temperature for several days. The precipitate that separated was collected on a filter, and recrystallized from ethanol several times, giving d,l-1-[3-(acetylthio)-2-methyl-1-oxopropyl]-2,3-dihydro-1H-indole-2-carboxylic acid, dicyclohexylamine salt (1.66 g.) with m.p. 201°–203°. The latter product is the diastereoisomer of the product which isolated first and melted at 218°–220°.

Analysis for: $C_{15}H_{17}NO_4S.C_{12}H_{23}N$: Calculated: C, 66.36; H, 8.25; N, 5.73: Found: C, 66.41; H, 8.41; N, 5.66.

EXAMPLE 20 d,l-1-[3-(acetylthio)-2-methyl-1-oxopropyl]-2,3-dihydro-1H-indole-2-carboxylic acid Treatment of d,l-1-[3-(acetylthio)-2-methyl-1-oxopropyl]-2,3-dihydro-1H-indole-2-carboxylic acid, dicyclohexylamine salt from Example 19 with a m.p. 218°–220° (1.93 g.) with 5% aqueous potassium hydrogen sulfate solution as described in Example 15 afforded the titled compound (0.6 g.) which melted at 125°–126°. The product was purified by recrystallizations from ethyl acetate and hexane.

Analysis for: $C_{15}H_{17}NO_4S$: Calculated: C, 58.61; H, 5.58; N, 4.56: Found: C, 58.39; H, 5.59; N, 4.51.

EXAMPLE 21 d,l-1-[3-(Acetylthio)-2-methyl-1-oxopropyl]-2,3-dihydro-1H-indole-2-carboxylic acid, the racemic diastereoisomer of Example 20

The title compound was obtained from d,l-1-[3-(acetylthio)-2-methyl-1-oxopropyl]-2,3-dihydro-1H-indole-2-carboxylic acid, dicyclohexylamine salt from Example 19 with m.p. 201°–203° by the treatment with 5% aqueous potassium hydrogen sulfate solution as described in Example 15. The product, purified by recrystallization from ether and hexane, melted at 94.5°–96°.

Analysis for: $C_{15}H_{17}NO_4S$: Calculated: C, 58.61; H, 5.58; N, 4.56: Found: C, 58.93; H, 5.66; N, 4.37.

EXAMPLE 22

2,3-Dihydro-5-methoxy-1H-indole-2-carboxylic acid ethyl ester

A three neck 3-liter round bottom flask equipped with a mechanical stirrer, water condenser, and a gas inlet tube was charged with 500 ml. of absolute ethanol and chilled in a dry ice-acetone bath. Dry hydrogen chloride gas was added at a rapid rate for 0.5 hours. Fifty grams of 5-methoxyindole-2-carboxylic acid ethyl ester (B. Heath-Brown and P. G. Philpott, J. Chem. Soc. 1965, 7185) followed by 100 g. of tin metal (30 mesh) were added to the solution with stirring. With the dry ice bath in place, but with no additional cooling the reaction mixture was stirred gently for 6 hours. The crystalline solid that separated was removed by filtration. The mother liquor was evaporated under reduced pressure to give an oil. The oil dissolved in 500 ml. of absolute ethanol, was placed in a 3-liter round bottom flask equipped with a stirrer and thermometer, and chilled to 10°. Gaseous ammonia was bubbled into the mixture until the pH was 9 (by wet pH paper) and the mixture was allowed to stand at 10° for one hour. The white precipitate was filtered and the filtrate was evaporated on a rotary evaporator to dryness. The initial white precipitate and the residue from the evaporation were combined and triturated repeatedly with warm ether. The combined ether triturates were washed with a sodium chloride solution (a water: saturated salt solution, 1:1) with vigorous shaking; whereupon most of the basic tin salts were suspended and separated in the aqueous phase. Both phases were filtered through Celite and separated. The ether solution was dried over magnesium sulfate and evaporated under reduced pressure on the rotary evaporator. The oily residue was dried in vacuo to give 22 g. of d,l-2,3-dihydro-5-methoxy-1H-indole-2-carboxylic acid ethyl ester.

Analysis for: $C_{12}H_{15}NO_3$: Calculated: C, 65.14; H, 6.83; N, 6.33: Found: C, 64.70; H, 6.75; N, 6.32.

EXAMPLE 23

2,3-Dihydro-5-methoxy-1-(2-methyl-1-oxo-2-propenyl)-1H-indole-2-carboxylic acid ethyl ester By substituting 2,3-dihydro-5-methoxy-1H-indole-2-carboxylic acid ethyl ester for 2,3-dihydro-indole-2-carboxylic acid ethyl ester in the procedure of Example 1, 2,3-dihydro-5-methoxy-1-(2-methyl-1-oxo-2-propenyl)-1H-indole-2-carboxylic acid ethyl ester was obtained as a thick oil.

Analysis for: $C_{16}H_{19}NO_4$: Calculated: C, 66.42; H, 6.62; N, 4.84: Found: C, 66.25; H, 6.65; N, 4.70.

EXAMPLE 24

2,3-Dihydro-5-methoxy-1-(2-methyl-1-oxo-2-propenyl)-1H-indole-2-carboxylic acid

To a solution of 2,3-dihydro-5-methoxy-1-(2-methyl-1-oxo-2-propenyl)-1H-indole-2-carboxylic acid ethyl ester from Example 23 (8.5 g.) in 45 ml. of reagent-grade methanol was added a solution of 1.32 g. of sodium hydroxide (98% purity) in 16 ml. distilled water with hand swirling. This reaction mixture was stirred at room temperature for 2 hours. With vigorous mechanical stirring, the reaction solution was poured into brine and the slightly turbid mass was acidified with concentrated hydrochloric acid. The resulting mixture was stirred, chilled in an ice-water-salt-bath for one hour and the solids were collected on a sintered-glass funnel and washed twice with cold water, to give 2,3-dihydro-5-methoxy-1-(2-methyl-1-oxo-2-propenyl)-1H-indole-2-carboxylic acid (7.32 g., m.p. 108°–111°). Recrystallization from ethyl acetate improved the m.p. to 115°–118°.

Analysis for: $C_{14}H_{15}NO_4$: Calculated: C, 64.35; H, 5.79; N, 5.36: Found: C, 63.89; H, 5.76; N, 5.22.

EXAMPLE 25

1-[3-(Benzoylthio)-2-methyl-1-oxopropyl]-5-methoxy-2,3-dihydro-1H-indole-2-carboxylic acid, dicyclohexylamine salt 2,3-Dihydro-5-methoxy-1-(2-methyl-1-oxo-2-propenyl)-1H-indole-2-carboxylic acid from Example 24 (2.61 g.) was added to a stirring mixture of 4-dimethylaminopyridine (0.122 g.), thiobenzoic acid (95% purity, 1.6 g.), and acetone (70 ml.) under a nitrogen atmosphere. The reaction mixture was heated at reflux for 8 hours and then chilled in a freezer. The precipitate was removed by filtration. The filtrate was evaporated on a rotary evaporator under reduced pressure to give a resinous material. The residue was dissolved in methylene chloride, and the methylene chloride solution was washed twice with 1 N cold hydrochloric acid, then twice with saline, and dried over anhydrous sodium sulfate. Evaporation of the methylene chloride solution on a rotary evaporator under reduced pressure gave a resinous material which was dissolved in acetonitrile. Dicyclohexylamine was added dropwise to the chilled acetonitrile solution until the pH of the solution reached to approximately 8. The resulting mixture was chilled in ice, and a precipitate was collected on a filter, and washed with acetonitrile. Recrystallization of the filter residue from ethanol gave 1-[3-(benzoylthio)-2-methyl-1-oxopropyl]-5-methoxy-2,3-dihydro-1H-indole-2-carboxylic acid, dicyclohexylamine salt (0.9 g.) which melted at 204°–206°.

Analysis for: $C_{21}H_{21}NO_5S \cdot C_{12}H_{23}N$: Calculated: C, 68.24; H, 7.64; N, 4.82: Found: C, 68.28; H, 7.62; N, 4.95.

EXAMPLE 26

1-[3-(Benzoylthio)-2-methyl-1-oxopropyl]-5-methoxy-2,3-dihydro-1H-indole-2-carboxylic acid The title compound was prepared from the corresponding dicyclohexylamine salt obtained in Example 25 (m.p. 204°–206°) by treatment with 5% aqueous potassium hydrogen sulfate solution as described in Example 15.

EXAMPLE 27

2,3-Dihydro-1-(3-mercapto-2-methyl-1-oxopropyl)-5-methoxy-1H-indole-2-carboxylic acid The title compound was prepared from 1-[3-(benzoylthio)-2-methyl-1-oxopropyl]-5-methoxy-2,3-dihydro-1H-indole-2-carboxylic acid of Example 26 by treatment with methanolic ammonia as described in Example 5.

EXAMPLE 28

2,3-Dihydro-5-methoxy-1-(1-oxo-2-propenyl)-1H-indole-2-carboxylic acid ethyl ester By substituting 2,3-dihydro-5-methoxy-1H-indole-2-carboxylic acid ethyl ester for 2,3-dihydro-1H-indole-2-carboxylic acid ethyl ester in the procedure for Example 6, 2,3-dihydro-5-methoxy-1-(1-oxo-2-propenyl)-1H-indole-2-carboxylic acid ethyl ester was prepared.

Analysis for: $C_{15}H_{17}NO_4$: Calculated: C, 65.44; H, 6.22; N, 5.09: Found: C, 65.45; H, 6.14; N, 4.89.

EXAMPLE 29

2,3-Dihydro-5-methoxy-1-(1-oxo-2-propenyl)-1H-indole-2-carboxylic acid

By substituting 2,3-dihydro-5-methoxy-1-(1-oxo-2-propenyl)-1H-indole-2-carboxylic acid ethyl ester from Example 28 for 2,3-dihydro-5-methoxy-1-(2-methyl-1-oxo-2-propenyl)-1H-indole-2-carboxylic acid ethyl ester in the procedure for Example 24, the titled compound was obtained.

EXAMPLE 30

1-[3-(Benzoylthio)-1-oxo-propyl]-2,3-dihydro-5-methoxy-1H-indole-2-carboxylic acid By substituting 2,3-dihydro-5-methoxy-1-(1-oxo-2-propenyl)-1H-indole-2-carboxylic acid from Example 29 for 2,3-dihydro-1-(1-oxo-2-propenyl)-1H-indole-2-carboxylic acid in the procedure of Example 8, the titled compound was prepared.

EXAMPLE 31

2,3-Dihydro-1-(3-mercapto-1-oxopropenyl)-5-methoxy-1H-indole-2-carboxylic

The titled compound was prepared from 1-[3-(benzoylthio)-1-oxopropyl]-2,3-dihydro-5-methoxy-1H-indole-2-carboxylic acid from Example 30 by treatment with methanolic ammonia as described in Example 4.

EXAMPLE 32

5-Chloro-2,3-dihydro-1H-indole-2-carboxylic acid ethyl ester

By substituting 5-chloroindole-2-carboxylic acid ethyl ester (B. Heath-Brown and P. G. Philpott, J. Chem. Soc., 1965, 7185) for 5-methoxyindole-2-carboxylic acid ethyl ester in the procedure of Example 22, 5-chloro-2,3-dihydro-1H-indole-2-carboxylic acid ethyl ester (m.p. 51°–53°) was prepared.

Analysis for: $C_{11}H_{12}ClNO_2$: Calculated: C, 58.54; H, 5.36; N, 6.21: Found: C, 58.57; H, 5.23; N, 6.31.

EXAMPLE 33

5-Chloro-2,3-dihydro-(2-methyl-1-oxo-2-propenyl)-1H-indole-2-carboxylic acid ethyl ester By substituting 5-chloro-2,3-dihydro-1H-indole-2-carboxylic acid ethyl ester from Example 32 for 2,3-dihydroindole-2-carboxylic acid ethyl ester in the procedure of Example 1, 5-chloro-2,3-dihydro-(2-methyl-1-oxo-2-propenyl)-1H-indole-2-carboxylic acid ethyl ester was obtained as an oil.

Analysis for: $C_{15}H_{16}ClNO_3$: Calculated: C, 61.33; H, 5.49; N, 4.77: Found: C, 60.94; H, 5.60; N, 4.64.

EXAMPLE 34

5-Chloro-2,3-dihydro-1-(2-methyl-1-oxo-2-propenyl)-1H-indole-2-carboxylic acid

By substituting 5-chloro-2,3-dihydro-1-(2-methyl-1-oxo-2-propenyl)-1H-indole-2-carboxylic acid ethyl ester from Example 33 for 2,3-dihydro-5-methoxy-1-(2-methyl-1-oxo-2-propenyl)-1H-indole-2-carboxylic acid ethyl ester in the procedure of Example 24, 5-chloro-2,3-dihydro-1-(2-methyl-1-oxo-2-propenyl)-1H-indole-2-carboxylic acid was prepared.

EXAMPLE 35

1-[3-(Benzoylthio)-2-methyl-1-oxopropyl]-5-chloro-2,3-dihydro-1H-indole-2-carboxylic acid By substituting 5-chloro-2,3-dihydro-1-(2-methyl-1-oxo-2-propenyl)-1H-indole-2-carboxylic acid from Example 34 for 2,3-dihydro-5-methoxy-1-(2-methyl-1-oxo-2-propenyl)-1H-indole-2-carboxylic acid in the procedure of Example 25, 1-[3-(benzoylthio)-2-methyl-1-oxopropyl]-5-chloro-2,3-dihydro-1H-indole-2-carboxylic acid, dicyclohexylamine was obtained. The latter salt was then treated with 5% aqueous potassium hydrogen sulfate as in Example 15 to give the titled compound.

EXAMPLE 36

5-Chloro-2,3-dihydro-1-(3-mercapto-2-methyl-1-oxopropyl-1H-indole-2-carboxylic acid Treatment of 1-[3-(benzoylthio)-2-methyl-1-oxopropyl]-5-chloro-2,3-dihydro-1H-indole-2-carboxylic acid from Example 35 with methanolic ammonia as described in Example 4, gave the titled compound.

EXAMPLE 37

2,3-Dihydro-1H-indole-2-carboxylic acid

METHOD A 2,3-Dihydro-1H-indole-2-carboxylic acid ethyl ester (19.1 g.) was partly dissolved in methanol (200 ml.) at room temperature. An aqueous potassium hydroxide solution obtained by dissolving 6.56 g. of KOH pellets (86% purity) in 70 ml. of water was added to the methanolic solution. The resulting solution was stirred under nitrogen atmosphere at room temperature for 1.5 hours. The reaction mixture was concentrated on a rotary evaporator under reduced pressure to approximately 100 ml., then transferred into an Erlenmeyer flask. The chilled solution was acidified first with chilled concentrated, then with dilute hydrochloric acid to pH ca. 5. Scratching of the resulting mixture while chilling caused separation of a precipitate which was collected on a filter and washed with cold water repeatedly to give 12.7 g. (76% yield) the product, m.p. 165°-170° dec.

Analysis for: $C_9H_9NO_2.\frac{1}{4}H_2O$ (167.67): Calculated: C, 64.47; H, 5.71; N, 8.35: Found: C, 64.64; H, 5.78; N, 8.25.

METHOD B

A mixture of 2,3-dihydro-1H-indole-2-carboxylic acid ethyl ester (9.56 g.), 80% aqueous DMSO-(250 ml.) and potassium hydroxide (86% pellets, 3.26 g.) was allowed to stir under nitrogen atmosphere at room temperature overnight, then evaporated on a rotary evaporator under vacuum to give a thick oily residue. The residue was dissolved in water (100 ml.). Several drops of 2 N aq NaOH solution was added to the solution to make it slightly alkaline. The aqueous solution was washed with ether several times to remove any unreacted starting material, then acidified while chilling in ice first with concentrated, then with dilute hydrochloric acid to pH ca. 5, whereby a precipitate separated. The mixture was chilled in ice, the precipitate was collected on a filter and washed with cold water. The product thus obtained melted at 176°-179° dec. and weighed 8.73 g. (100%).

Analysis for: $C_9H_9NO_2.1/6H_2O$ (166.17): Calculated: C, 65.05; H, 5.66; N, 8.43: Found: C, 65.23; H, 5.67; N, 8.28.

EXAMPLE 38

R-3-Benzoylthio-2-methylpropanoyl Chloride

To a stirred mixture of thionyl chloride (30 ml., Aldrich Chemical Co.) and 1-S-3-benzoylthio-2-methylpropanoic acid (13.44 g.) in a 100 ml. round bottom flask capped with a calcium chloride drying tube was added two drops of triethylamine. The stirring was continued at room temperature for 7 hours, and the reaction mixture was evaporated on a rotary evaporator under reduced pressure. The liquid residue thus obtained was kept under high vacuum for several hours.

EXAMPLE 39

1-(S)-1-[(S)-3-(Benzoylthio)-2-methyl-1-oxopropyl]-2,3-dihydro-1H-indole-2-carboxylic acid (Method B)

To a stirred suspension of 2,3-dihydro-1H-indole-2-carboxylic acid (9.79 g.) in methylene chloride (250 ml.) was added triethylamine (12.3 g.). The clear solution thus obtained was chilled in ice. R-3-Benzoylthio-2-methylpropanoyl chloride (the entire amount obtained from 13.44 g. of the corresponding acid in Example 38) dissolved in 50 ml. of methylene chloride was added slowly under vigorous stirring. The ice-bath was removed in 15 minutes, and the stirring was continued for 2.5 hours. The reaction mixture was washed with 5% aqueous potassium hydrogen-sulfate solution 3 times (250 ml., 200 ml. and 150 ml.), then with saline (twice), and dried over anhydrous sodium sulfate. Evaporation of the methylene chloride on a rotary evaporator under reduced pressure (in a large round bottom flask) gave a resinous residue which was kept under high vacuum for ca. 1 hour. The residue was dissolved in acetonitrile (150 ml.), and the solution was chilled. Dicyclohexylamine (DCHA, 11 g., to pH 7.5-8.0) was added slowly with good stirring to the cold solution, and the resulting mixture was kept in a refrigerator for 1.5 hours. The precipitate was collected on a filter, and the filter residue was washed with acetonitrile repeatedly. The DCHA salt melted at 212.5°-215°, and weighed 16.1 g. (98% of theory). Recrystallization from ethanol improved the m.p. to 219°-221°, giving 12.49 g. of the product, $\alpha]_D^{24.5} = -68.93$ (c=1.15%, EtOH).

Analysis for: $C_{20}H_{19}NO_4S.C_{12}H_{23}N$: Calculated: C, 69.78; H, 7.69; N, 5.09: Found: C, 69.38; H, 7.58; N, 5.26.

The salt (38.0 g.) was powdered in a mortar and pestle to fine particles, and shaken vigorously with aqueous 5% KHSO$_4$ solution (450 ml.) and ethyl acetate (200 ml.) in a separatory funnel. The ethyl acetate layer was collected and the aqueous layer was extracted with ethyl acetate two more times using 150 ml. and 100 ml. each time. The combined ethyl acetate extracts were washed with water, then with saline, and dried over anhydrous sodium sulfate (or magnesium sulfate). The ethyl acetate was evaporated on a rotary evaporator under reduced pressure. In the later states of the evaporation the concentrated solution was seeded with the product of Example 15, and the evaporation was continued to dryness whereby a crystalline product was obtained as a large mass. The mass was broken into small pieces and dissolved in ca. 100 ml. of hot ethyl acetate. The filtered solution was diluted with hexane until it became cloudy, and was first chilled in ice then in a freezer. The precipitate was collected on a filter and washed with anhydrous ether giving 21.6 g. of 1-(S)-1-[(S)-3-(benzoylthio)-2-methyl-1-oxopropyl]-2,3-dihydro-1H-indole-2-carboxylic acid, m.p. 140.5°–142°, $[\alpha]_D^{25} = -184.9$ (c=1.156%, EtOH). TLC obtained on a precoated Silica gel 60F-254 (available from Brinkmann) by developing with a solution of $CH_2Cl_2(8)/EtOH(2)/Toluene(1)/NEt_3(1)$ showed a spot at Rf 0.635 when detected under UV light. The diastereomer from the reaction showed its spot at Rf 0.54.

Analysis for: $C_{20}H_{19}NO_4S$ (369.42): Calculated: C, 65.02; H, 5.18; N, 3.79: Found: C, 65.05; H, 5.04; N, 3.81.

EXAMPLE 40

1-(S)-2,3-Dihydro-1-[(S)-3-mercapto-2-methyl-1-oxopropyl]-1H-indole-2-carboxylic acid A mixture of 1-1-[3-(benzoylthio)-2-methyl-1-oxopropyl]-2,3-dihydro-1H-indole-2-carboxylic acid (5.0 g.) and 2-methoxyethylamine (40 ml.) in a 500 ml. round bottom flask was stirred under nitrogen atmosphere for 15 minutes at 0°, then for 10 minutes at room temperature. The excess amine was evaporated on a rotary evaporator under reduced pressure to give an oil which was kept under high vacuum for 15 minutes. The residue was dissolved in ca. 200 ml. of cold oxygen-free water, and the aqueous solution was washed with freshly opened anhydrous ether 3 times. Immediately (to avoid disulfide formation in alkaline conditions), the aqueous layer was acidified with dilute hydrochloric acid to pH ca. 1. The oily product thus separated was extracted with ether 3 times (150 ml., 100 ml., and 50 ml. in each extraction). The combined ether extracts were washed with saline 3 times and dried over anhydrous sodium sulfate for 1 hour. The ether was evaporated on a rotary evaporator under reduced pressure, and the residue was kept under high vacuum for 20 minutes. The solid product thus obtained was dissolved in ca. 30 ml. of hot ethyl acetate. The ethyl acetate solution was transferred quantitatively to filter paper using a pipette and was carefully filtered using Reeve Angel filter paper. The filtrate was diluted with hexane until it became cloudy (total volume of hexane used for the dilution was approximately 110 ml), and kept at room temperature for 1 hour, then chilled in ice for several hours. The precipitate was collected on a filter and washed with a mixture of ethyl acetate and hexane (3:10 by volume), giving 2.95 g. (82%) of 1-(S)-2,3-dihydro-1-[(S)-3-mercapto-2-methyl-1-oxopropyl]-1H-indole-2-carboxylic acid, which melted at 140.5°–142°, $[\alpha]_D^{24} = -178.1$ (c=1.35%, EtOH). TLC obtained as previously described showed a spot at Rf 0.45. There was also a very faint spot at Rf 0.25, which is believed to come from a trace amount of the disulfide impurity.

Analysis for: $C_{13}H_{15}NO_3S$ (265.3): Calculated: C, 58.84; H, 5.70; N, 5.28: Found: C, 58.65; H, 5.73; N, 5.46.

EXAMPLE 41 d,l-3,4,11,11a-Tetrahydro-4-methyl-1H,5H-[1,4]thiazepino[4,3-a]indole-1,5-dione d,l-2,3-Dihydro-1-(3-mercapto-2-methyl-1-oxopropyl)-1H-indole-2-carboxylic acid (1.247 g.) from Example 4 was dissolved in dry methylene chloride (700 ml.), and the resulting solution was chilled in ice and stirred under nitrogen atmosphere. To this solution was added 4-dimethylaminopyridine (60 mg.), and the resulting mixture was stirred for 5 minutes. Dicyclohexylcarbodiimide (1.02 g.) dissolved in ca. 10 ml. of methylene chloride was added, and the stirred reaction mixture was chilled in ice for 15 minutes, then allowed to warm room temperature and stirred for 4 hours. The reaction mixture was concentrated on a rotary evaporator under reduced pressure to approximately 100 ml. and chilled in dry ice-acetone. The precipitate that separated was collected on a filter, and washed with methylene chloride. The combined filtrate and washings were evaporated on a rotary evaporator under reduced pressure to give an oily residue which solidified on standing. The solid material was recrystallized from ether to give 3,4,11,11a-tetrahydro-4-methyl-1H,5H-[1,4]-thiazepino[4,3-a]indole-1,5-dione (0.7 g.), m.p. 108°–110°.

Analysis for: $C_{13}H_{13}NO_2S$: Calculated: C, 63.13; H, 5.30; N, 5.66: Found: C, 63.29; H, 5.11; N, 5.73.

EXAMPLE 42 d,l-3,4,11,11a-Tetrahydro-4-methyl-1H,5H-[1,4]thiazepino[4,3-a]-indole-1,5-dione Treatment of d,l-2,3-dihydro-1-(3-mercapto-2-methyl-1-oxopropyl)-1H-indole-2-carboxylic acid from Example 5 which is diastereoisomeric with the starting material used in Example 41 with dicyclohexylcarbodiimide according to the procedure of Example 41 gives d,l-3,4,11,11a-tetrahydro-4-methyl-1H,5H-[1,4]-thiazepino[4,3-a]indole-1,5-dione which is the diastereoisomer of the compound described in Example 41.

EXAMPLE 43

(4S,11aS)-3,4,11,11a-Tetrahydro-4-methyl-1H,5H-[1,4]-thiazepino-[4,3-a]indole-1,5-dione By substituting 1-(S)-2,3-dihydro-1-[(S)-mercapto-2-methyl-1-oxopropyl]-1H-indole-2-carboxylic acid for 2,3-dihydro-1-(3-mercapto-2-methyl-1-oxopropyl)-1H-indole-2-carboxylic acid in the procedure for Example 41, (4S, 11aS)-3,4,11,11a-tetrahydro-4-methyl-1H,5H-[1,4-thiazepino[4,3-a]indole-1,5-dione was obtained.

EXAMPLE 44

(4R,11aS)-3,4,11,11a-Tetrahydro-4-methyl-1H,5H-[1,4-thiazepino-[4,3a]indole-1,5-dione By substituting d-(S)-2,3-dihydro-1-[(R)-mercapto-2-methyl-1-oxopropyl]-1H-indole-2-carboxylic acid for 2,3-dihydro-1-(3-mercapto-2-methyl-1-oxopropyl)-1H-indole-2-carboxylic acid in the procedure of Example 41, (4R, 11aS)-3,4,11,11a-tetrahydro-4-methyl-1H,5H-[1,4]thiazepino[4,3-a]indole-1,5-dione was obtained.

EXAMPLE 45

(4S,11aR)-3,4,11,11a-Tetrahydro-4-methyl-1H,5H-[1,4]thiazepino-[4,3-a]indole-1,5-dione By substituting 1-(R)-2,3-dihydro-1-[(S)-mercapto-2-methyl-1-oxopropyl]-1H-indole-2-carboxylic acid for 2,3-dihydro-1-(3-mercapto-2-methyl-1-oxopropyl)-1H-indole-2-carboxylic acid in the procedure of Example 41, (4S,11aR)-3,4,11,11a-tetrahydro-4-methyl-1H,5H-[1,4]thiazepino[4,3-a]indole-1,5-dione was obtained.

EXAMPLE 46

(4R,11R)-3,4,11,11a-Tetrahydro-4-methyl-1H,5H-[1,4]-thiazepino-[4,3-a]indole-1,5-dione By substituting 1-(R)-2,3-dihydro-1-[(R)-mercapto-2-methyl-1-oxopropyl]-1H-indole-2-carboxylic acid for 2,3-dihydro-1-mercapto-2-methyl-1-oxopropyl)-1H-2-carboxylic acid in the procedure of Example 41, (4R,11aR)-3,4,11,11a-tetrahydro-4-methyl-1H,5H-[1,4]thiazepino[4,3-a]indole-1,5-dione was obtained.

EXAMPLE 47

3,4,11,11a-Tetrahydro-1H,5H-[1,4]thiazepino[4,3-a]indole-1,5-dione

By substituting 2,3-dihydro-1-(3-mercapto-1-oxopropyl)-1H-indole-2-carboxylic acid for 2,3-dihydro-(3-mercapto-2-methyl-1-oxopropyl)-1H-indole-2-carboxylic acid in the procedure of Example 41, 3,4,11,11a-tetrahydro-1H,5H-[1,4]thiazepino[4,3-a]-indole-1,5-dione was prepared.

EXAMPLE 48

Similarly the following compounds are prepared.
9-Methoxy-3,4,11,11a-tetrahydro-4-methyl-1H,5H-[1,4]thiazepino-[4,3-a]indole-1,5dione
9-Chloro-3,4,11,11a-tetrahydro-4-methyl-1H,5H-[1,4]thiazepino-[4,3-a]indole-1,5-dione.

EXAMPLE 49 l-3-Benzoylthio-2-methyl propanoic acid

A solution of d-dehydroabietylamine [prepared from d-dehydroabietylamine acetate (127 g; 0.368 moles), triethylamine (39.2 g, 54 ml, 0.387 moles), water (75 ml) and ethyl acetate (1500 ml) at 50°–55°] was cooled to 45° C. and added as rapidly as possible at 30° C. to a solution of d,l-3-benzoylthio-2-methylpropionic acid (150 g, 0.66 moles) in ethyl acetate (1500 ml). The temperature rose to 40° C., the solution was seeded, cooled to 30° C. over 30 minutes, then to 20° C. over 30 minutes. The solid was filtered, slurried with ethyl acetate (500 ml), refiltered, and washed with ethyl acetate (75 ml). The wet cake was dissolved in ethanol 3A anhydrous (3000 ml) at 70°–75° C. for five minutes, filtering off any insolubles, cooled to 20° C. and allowed to stand one hour. The precipitate solid was filtered and dried in a vacuum oven at 35° C. to constant weight to provide the pure l-3-benzoylthio-2-methyl propanoic acid, d-dehydroabietyl-amine salt (93.0 g), m.p. 153°–153.5°, $[\alpha]_D^{25} = +16.2°$ (C=2, THF), 54.5% yield.

The l-3-benzoylthio-2-methyl propanoic acid, d-dehydroabietylamine salt (100 g, 0.196 moles) was partitioned between methylene chloride (400 ml) and 1N-aqueous sodium hydroxide (200 ml., 0.2 mole) and the liquids filtered to break the emulsion formed. The methylene chloride layer was separated and washed with water (100 ml.). The aqueous layers were combined and washed with methylene chloride (100 ml.). The aqueous layer was brought to pH 3 with 1N-aqueous hydrochloric acid, and the precipitated oil extracted with methylene chloride (150 ml. and 50 ml.). The dry methylene chloride extract was diluted with hexane (400 ml.) and the solution was concentrated with stirring to 400 ml. not exceeding 35°–40° C. The mixture was cooled with stirring at 20°–25° C. for one hour.

Filtration, washing with hexane (2×25 ml.) and drying in a vacuum oven (below 35° C.) provided 1-3-benzoylthio-2-methylpropanoic acid (36.6 g.) (83.2% yield), m.p. 68.5°–69.5° C., $[\alpha]_D^{25} = -42.4°$ (C=2 in EtOH).

EXAMPLE 50

(S)-Phthaloylalanyl Chloride

A mixture of (S)-phthaloylalanine (32.88 g.), thionyl chloride (75 ml.), and triethylamine (4 drops) were stirred at room temperature overnight, then evaporated on a rotary evaporator under reduced pressure. The residue was dissolved in anhydrous ether, and the ether solution was evaporated on a rotary evaporator under reduced pressure to give an oily residue. The dissolution of the residue in anhydrous ether followed by evaporation was repeated two additional times. The oily residue solidified slowly at room temperature. The crystalline solid was placed in a high vacuum for several hours. The product melted at 51°–53°; $[\alpha]_D^{27} = -8.34$ (c=1.04% CHCl$_3$).

EXAMPLE 51

(S)-2,3-Dihydro-1-[(S)-2-(1,3-Dihydro-1,3-Dioxo-2H-Isoindol-2yl)-1-Oxopropyl]-1H-Indole-2-Carboxylic Acid, Dicyclohexylamine (S)-Phthaloylalanyl chloride (the entire amount from the previous example, 0.15 mole) dissolved in a small amount of dry methylene chloride (60 ml.) was added over 10 min. to a chilled (0° C.), rapidly stirred solution of 2,3-dihydroindole-2-carboxylic acid (24.5 g., 0.15 mole), triethylamine (30.7 g., 0.3 mole), and methylene chloride (700 ml.) under nitrogen atmosphere. The resulting mixture was stirred at 0° C. for an additional 15 min., then at room temperature for 2 hr. The reaction mixture was washed with 5% aqueous potassium bisulfate solution 3 times (600 ml., 500 ml., and 400 ml.), then with saline twice, and dried over sodium sulfate. Evaporation of methylene chloride on a rotary evaporator under reduced pressure gave an amorphous solid which was dried in a high vacuum for several hours, giving a crude product (59 g.) as a diastereoisomeric mixture in the ratio of 6:4.

The product was dissolved in acetonitrile (300 ml.), then cooled to about 10° C. Dicyclohexylamine (27 g.) was added slowly to the acetonitrile solution with vigorous stirring. The resulting mixture was allowed to stand at room temperature for 1.5 hr., then in a refrigerator for 0.5 hr. The precipitate that separated was collected on a filter, and washed with acetonitrile (6 or 7 times with a total of 200 ml.), giving 28.0 g. of partially resolved product, m.p. 199°–201.5° C. $[\alpha]_D^{28} = -143.3°$ (c=1.12%, EtOH).

The product was dissolved in approximately 150 ml. of hot ethanol. The solution was allowed to cool to room temperature and then chilled in a refrigerator for 1–2 hours. The precipitate was collected on a filter and washed with chilled ethanol several times, then with acetonitrile several times. The product thus obtained melted at 201°–203° C., and weighed 21.25 g., $[\alpha]_D^{28} = -150.1°$ (c=1.01%, EtOH). Analytical sample melted at 204.5°–206.5° C.; $[\alpha]_D^{25} = -156.45°$ (c=0.6%, EtOH).

Analysis for: $C_{20}H_{16}N_2O_5 \cdot C_{12}H_{23}N$: Calculated: C, 70.45; H, 7.20; N, 7.70: Found: C, 70.26; H, 7.05; N, 7.70.

EXAMPLE 52

(R)-2,3-Dihydro-1-[(S)-2-(1,3-Dihydro-1,3-Dioxo-2H-Isoindol-2-yl)-1-Oxopropyl]-1H-Indole-2-Carboxylic Acid, Dicyclohexylamine Combined acetonitrile filtrate and washings from the previous example (Example 51) were filtered to remove a small amount of a precipitate, and evaporated on a rotary evaporator to dryness to give 27 g. of amorphous solid, $[\alpha]_D^{25} = -8.01°$ (c=1.15%, EtOH).

Analysis for: $C_{20}H_{16}N_2O_5.C_{12}H_{23}N$: Calculated: C, 70.43; H, 7.20; N, 7.70: Found: C, 70.30; H, 7.29; N, 7.62.

EXAMPLE 53

(S)-2,3-Dihydro-1-[(S)-2-(1,3-Dihydro-1,3-Dioxo-2H-Isoindol-2-yl)-1-Oxopropyl]-1H-Indole-2-Carboxylic Acid, Hemiethyl Acetate Dicyclohexylamine salt (25.9 g.) of the title compound was shaken with 5% aqueous potassium bisulfate solution (400 ml.), and the free acid was extracted three times with ethyl acetate (total volume 550 ml.).

The combined extracts were washed with saturated aqueous sodium chloride solution twice, and dried over anhydrous sodium sulfate. Evaporation of the ethyl acetate on a rotary evaporator under reduced pressure, then in vacuo gave an amorphous solid (20 g.), $[\alpha]_D^{25} = -250.01°$ (c=1.165%, EtOH), ms (C.I): m/e 265. Analysis for: $C_{20}H_{16}N_2O_5.\frac{1}{2}EtOAc$: Calculated: C, 64.70; H, 4.94; N, 6.86: Found: C, 64.58; H, 4.84; N, 7.01.

EXAMPLE 54

(S)-1-[(S)-2-Amino-Oxopropyl]-2,3-Dihydro-1H-Indole-2-Carboxylic Acid (S)-2,3-Dihydro-1-[(S)-2-(1,3-dihydro-1,3-dioxo-2H-isoindol 2-yl)-1-oxopropyl]-1H-indole-2-carboxylic acid, dicyclohexylamine (20.4 g.) was treated with 5% aqueous potassium bisulfate solution (300 ml.), and the free acid that formed was extracted three times with methylene chloride (combined extracts 450 ml.). The combined extracts were washed with saline twice, then dried over anhydrous sodium sulfate. Evaporation of the methylene chloride on a rotary evaporator under reduced pressure, then in high vacuum gave an amorphous solid which was dissolved in methanol (200 ml.). Hydrazine (95%, 1.43 g.) was added to the methanol solution. The resulting mixture was stirred under nitrogen atmosphere at room temperature for 24 hr., then chilled in an ice-salt mixture for 3 hr. A precipitate (phthalhydrazide, 4.06 g.) was collected on a filter, and washed with methanol. The combined filtrate and washings were evaporated on a rotary evaporator under reduced pressure, then in vacuo to give a solid residue. The residue was triturated with methylene chloride (ca. 250 ml.) and filtered. The filter residue was washed with methylene chloride several times and dried in vacuo. The crude product was dissolved in water (ca. 50 ml.) at room temperature, and filtered. The filter residue was washed with water. The combined filtrate and washings were evaporated carefully on a rotary evaporator under reduced pressure to give a solid residue which was dried over phosphorous pentoxide in vacuo to give the title product (6.31 g.), $[\alpha]_D^{25} = -140.85$ (c=1.44%, water). The analytical sample which was obtained by recrystallizations from methanol melted at 171°-172° (when the melting point was determined with rapid heating, the compound melted at 206.5°-209°), $[\alpha]_D^{25} = -161.17°$ (c=1.065%, EtOH).

Analysis for: $C_{12}H_{14}N_2O_3$: Calculated: C, 61.52; H, 6.02; N, 11.96: Found: C, 61.44; H, 6.20; N, 12.26.

EXAMPLE 55

(−)-(S)-1-[(2S)-2-[[(1S)-1-(Ethoxycarbonyl)-3-Phenylpropyl]Amino]-1-Oxopropyl]-2,3-Dihydro-1H-Indole-2-Carboxylic Acid, Maleate A mixture of (S)-1-[(S)-2-amino-1-oxopropyl]-2,3-dihydro-1H-indole-2-carboxylic acid (2.34 g.), triethylamine (1.01 g.), 2-oxo-4-phenylbutanoic acid ethyl ester (2.6 g.), powdered molecular sieve 3A (10 g.), anhydrous ethanol (250 ml.) and Raney nickel (3.0 g.) was hydrogenated at room temperature using a Paar hydrogenator with 45 psi hydrogen pressure until uptake of hydrogen ceased. The reaction mixture was filtered through a bed of Celite, and the filter residue was washed with ethanol repeatedly. The combined filtrate and washings were evaporated on a rotary evaporator under reduced pressure to give a resinous residue. The residue was dissolved in a mixture of water (80 ml.) and ether (25 ml.), and the mixture was made alkaline to pH 9.6 by addition of dilute aqueous sodium hydroxide solution. The ether layer was separated and the aqueous layer was washed with ether two additional times. The aqueous solution was acidified to pH 4.2 by addition of dilute hydrochloric acid, then saturated with sodium chloride. The acidic aqueous solution was extracted with ethyl acetate 4 times. The combined extracts were dried over anhydrous sodium sulfate and evaporated on a rotary evaporator to dryness. The residue was dissolved in a small amount of ethyl acetate (ca. 5 ml.). Maleic acid (0.9 g.) was added to the solution and the resulting mixture was stirred at room temperature until a clear solution was obtained (ca. 1.5 hr.). Anhydrous ether (ca. 70 ml.) was added slowly with vigorous stirring until no additional milky precipitate separated. The mixture was chilled and the supernatant liquid was decanted. The residue was redissolved in a small amount of ethyl acetate. The solution was added dropwise to a large amount of anhydrous ether (ca. 3.5 l.), whereby most of the product was dissolved. The ether solution was filtered and the filtrate was evaporated on a rotary evaporator to ca. 150 ml., and chilled in ice for several hours. The supernatant liquid was decanted and the residue was dissolved in anhydrous ether (ca. 2 l.) with warming on a steam bath. The solution was concentrated on a rotary evaporator to ca. 100 ml. and chilled in ice. The supernatant liquid was decanted and collected separately (see following example). This recrystallization was repeated 8 more times to give the title product (210 mg.) as fine white powder. The compound did not have a definite melting point (melted at 69°-80°), and showed one spot on TLC (silica gel, $CH_2Cl_2(4)/MeOH$ (1)) with Rf 0.41, $[\alpha]_D^{25} = -84.6°$ (c=0.755%, MeOH).

Analysis for: $C_{24}H_{28}N_2O_5.C_4H_4O_4$: Calculated: C, 62.21; H, 5.97; N, 5.18: Found: C, 62.27; H, 5.97; N, 5.38.

EXAMPLE 56

(−)-(S)-1-[(2S)-2-[[(1R)-1-(Ethoxycarbonyl)-3-Phenylpropyl]Amino]-1-Oxopropyl]-2,3-Dihydro-1H-Indole-2-Carboxylic Acid, Maleate The ether decants from the previous example were combined and concentrated on a rotary evaporator to ca. 100 ml., and chilled in ice. The supernatant liquid was decanted and the residue was purified in the same fashion as described in the previous example to give the title product (360 mg.) as a very light white powder. The compound did not have a definite melting point and showed a spot on TLC (silica gel, $CH_2Cl_2(4)/MeOH(1)$) at Rf 0.48, $[\alpha]_D^{27} = -101.18°$ (c=0.99%, MeOH).

Analysis for: $C_{24}H_{29}N_2O_5 \cdot C_4H_4O_4$: Calculated: C, 62.21; H, 5.97; N, 5.18: Found: C, 62.87; H, 6.09; N, 5.48.

EXAMPLE 57

In the in vitro assay for angiotensin converting enzyme inhibition utilizing the rabbit lung extract according to the procedure of Cushman et al., Biochem. Pharmacol., 20, 1637–1648 (1971), the following results were obtained:

| Compound of Example | $IC_{50}$ |
|---|---|
| 54 | $3.1 \times 10^{-6}$ M |
| 55 | $1.18 \times 10^{-7}$ M |
| 56 | $9 \times 10^{-7}$ M |

EXAMPLE 58

When tested in the normotensive conscious rat according to the procedure of Rubin et al., J. Pharmacol. Exp. Ther., 204, 271–280 (1978), the compound of Example 55 inhibited the vasopressor action of Angiotensin I 46 percent 2 hours after being administered orally at a dose of 1 mg/kg. of body weight.

EXAMPLE 59

When administered orally in the spontaneously hypertensive rat, the compound of Example 55 showed the following reductions in blood pressure:

| Dose mg/kg. | Reduction of Systolic BP mm. Hg. | No. of Subjects |
|---|---|---|
| 2.5 | −13 | 4 |
| 5.0 | −23 | 4 |
| 10.0 | −33 | 4 |

What is claimed is:

1. A compound of the formula:

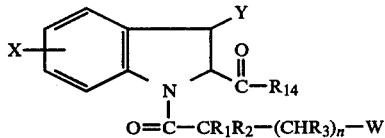

wherein:
n is 1 or 0;
$R_1$ is hydrogen, lower alkyl, aryl, or aralkyl;
$R_2$ is hydrogen or lower alkyl;
$R_3$ is hydrogen, lower alkyl or aroyl;
X is hydrogen, hydroxy, lower alkyl, lower alkoxy or halogen;
Y is hydrogen, lower alkyl or aryl;
$R_{14}$ is $R_4$ or OZ, where $R_5$ is hydroxy, amino, or lower alkoxy, and Z is a carboxylic acid protecting group; and
W is bromine, chlorine, iodine, or tosyloxy;
wherein aryl refers to phenyl or phenyl substituted by a halogen, lower alkyl, or lower alkoxy group; aralkyl refers to benzyl or benzyl substituted on the phenyl ring by a halogen, a lower alkyl or a lower alkoxy group; and aroyl refers to benzoyl or benzoyl substituted on the phenyl ring by a halogen, lower alkyl or lower alkoxy group.

2. A compound of claim 1 wherein W is bromine, chlorine or iodine.

3. A compound of claim 1 wherein $R_3$ is hydrogen or lower alkyl.

4. A compound of the formula:

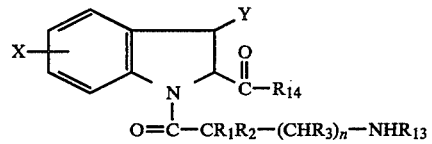

wherein:
n is 1 or 0;
$R_1$ is hydrogen, lower alkyl, aryl or aralkyl;
$R_2$ is hydrogen or lower alkyl;
$R_3$ is hydrogen, lower alkyl or aroyl;
X is hydrogen, hydroxy, lower alkyl, lower alkoxy or halogen;
Y is hydrogen, lower alkyl or aryl;
$R_{13}$ is hydrogen or lower alkyl; and
$R_{14}$ is $R_5$ or OZ, where $R_5$ is hydroxy, amino, or lower alkoxy, and Z is a carboxylic acid protecting group;
wherein aryl refers to phenyl or phenyl substituted by a halogen, lower alkyl, or lower alkoxy group; aralkyl refers to benzyl or benzyl substituted on the phenyl ring by a halogen, a lower alkyl or a lower alkoxy group; and aroyl refers to benzoyl or benzoyl substituted on the phenyl ring by a halogen, lower alkyl or lower alkoxy group.

5. A compound of claim 4 in which $R_2$ is hydrogen.
6. A compound of claim 4 in which n is 0.
7. A compound of claim 4 in which Y is hydrogen.
8. A compound of claim 4 in which $R_1$ is lower alkyl.
9. A compound of claim 4 in which $R_{13}$ is hydrogen.
10. A compound of claim 4 which is 1-[2-amino-1-oxopropyl]-2,3-dihydro-1H-indole-2-carboxylic acid.
11. A compound of claim 4 which is (S)-1-[(S)-2-amino-1-oxopropyl]-2,3-dihydro-1H-indole-2-carboxylic acid.

* * * * *